US006770626B2

(12) United States Patent
Ben-Sasson

(10) Patent No.: US 6,770,626 B2
(45) Date of Patent: Aug. 3, 2004

(54) TISSUE REMODELING

(75) Inventor: Shmuel Ben-Sasson, Jerusalem (IL)

(73) Assignees: Children's Medical Center Corporation, Boston, MA (US); Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 10/032,330

(22) Filed: Dec. 31, 2001

(65) Prior Publication Data

US 2002/0165150 A1 Nov. 7, 2002

Related U.S. Application Data

(63) Continuation-in-part of application No. PCT/US00/32852, filed on Dec. 4, 2000, and a continuation-in-part of application No. 09/161,094, filed on Sep. 25, 1998, now abandoned.

(51) Int. Cl.[7] .......................... A61K 38/08; C07K 7/06
(52) U.S. Cl. .......................... 514/15; 514/12; 514/13; 514/14; 514/16; 514/17; 530/327
(58) Field of Search .................. 514/9, 11, 12, 514/13, 14, 15, 16, 17; 530/317, 321, 324, 325, 326, 327, 328, 329, 330, 345

(56) References Cited

U.S. PATENT DOCUMENTS

| 5,200,327 A | 4/1993 | Garvin et al. ............... 435/69.5 |
| 5,200,510 A | 4/1993 | Kumar et al. ............... 530/383 |
| 5,250,516 A | 10/1993 | Urry ........................... 514/17 |
| 5,340,800 A | 8/1994 | Liu et al. ..................... 514/12 |
| 5,418,147 A | 5/1995 | Huang et al. ............... 435/69.1 |
| 5,439,887 A | 8/1995 | Hamon et al. ............... 514/13 |
| 5,470,828 A | * 11/1995 | Ballard et al. ............... 514/12 |
| 5,478,810 A | 12/1995 | Stuber et al. ............... 514/17 |
| 5,527,681 A | 6/1996 | Holmes ........................ 435/6 |
| 5,556,744 A | 9/1996 | Weiner et al. ............... 435/5 |

(List continued on next page.)

FOREIGN PATENT DOCUMENTS

| WO | WO 93/16703 A1 | 9/1993 |
| WO | WO 94/07913 A1 | 4/1994 |
| WO | WO 96/32411 A1 | 10/1996 |
| WO | WO 97/25341 A1 | 7/1997 |
| WO | WO 97/33908 A1 | 9/1997 |
| WO | WO 98/32017 A2 | 7/1998 |
| WO | WO-9853050 A2 | * 11/1998 |
| WO | WO-9853051 A1 | * 11/1998 |

OTHER PUBLICATIONS

Alem″ et al, "Differentiation of PC12 phaeochromocytoma cells induced by v–src oncogene", Nature 316:557–559 (1985).

Birchall et al, "Ro 32–0432, a Selective and Orally Active Inhibitor of Protein Kinase C Prevents T–Cell Activation", J. Pharmacol Exp Ther 268(2):922–929 (1994).

Bradshaw et al, "Therapeutic potential of protein kinase C Inhibitors", Agents Actions 38:135–147 (1993).

Dudek et al, "Regulation of Neuronal Survival by the Serine–Threonine Protein Kinase Akt", Science 275:661–665(1997).

(List continued on next page.)

Primary Examiner—Jeffrey Edwin Russel
(74) Attorney, Agent, or Firm—Browdy and Neimark, P.L.L.C.

(57) ABSTRACT

The invention concerns a method for the modulation of tissue-remodeling processes, by contacting the tissue to be remodeled with a compound comprising a sequence derived from certain regions of TGF-β super family Ser/Thr/kinase receptors.

2 Claims, 12 Drawing Sheets

U.S. PATENT DOCUMENTS

| | | | | |
|---|---|---|---|---|
| 5,594,105 A | | 1/1997 | Comoglio et al. | 530/326 |
| 5,688,513 A | | 11/1997 | Binger et al. | 424/271.1 |
| 5,693,325 A | | 12/1997 | Kahn | 424/188.1 |
| 5,763,198 A | | 6/1998 | Hirth et al. | 435/7.21 |
| 5,777,093 A | | 7/1998 | Shiloh et al. | 536/23.5 |
| 5,827,692 A | | 10/1998 | Tang et al. | 435/69.1 |
| 5,843,462 A | | 12/1998 | Conti-Fine | 424/245.1 |
| 5,891,640 A | | 4/1999 | DeLeys | 435/7.1 |
| 5,910,478 A | | 6/1999 | Hlavka et al. | 514/9 |
| 6,011,014 A | | 1/2000 | Andersen et al. | 514/15 |
| 6,017,883 A | | 1/2000 | Cooper, Jr. | 514/12 |
| 6,174,993 B1 | * | 1/2001 | Ben-Sasson | 530/326 |
| 6,228,989 B1 | | 5/2001 | Traugh et al. | 536/350 |
| 6,232,287 B1 | | 5/2001 | Ruoslahti et al. | 514/2 |
| 6,548,482 B1 | * | 4/2003 | Khosla et al. | 514/21 |

OTHER PUBLICATIONS

Franke et al, "P13K: Downstream AKTion Blocks Apoptosis", *Cell* 88:435–437 91997).

Freedman et al, "Desensitization of G Protein–Coupled Receptors", *Recent Prog Horm Res* 51:319–353 (1996).

Glover et al, "Polo Kinase: The Choreographer of the Mitotic Stage?", *J Cel Biol* 135(6)(2):1681–1684 (1996).

Hanks et al, "The Eukaryotic Protein Kinase Superfamily", *The Protein Kinase Facts Book*, vol. 1 (Hardie et al, eds), Academics Press, Chapter 2 (1995).

Hanks et al, "The eukaryotic protein kinase superfamily: kinase (catalytic) domain structure and classification", *FASEB J* 9:576–596 (1995).

Hemmings et al, "Akt Signaling: Linking Membrane Events to Life and Death Decisions", *Science* 275:628–631 (1997).

Hubbard et al, "Crystal structure of the tyrosine kinase domain of the human insulin receptor", *Nature* 372:746–753 (1994).

Hughes Al, "Evolution of the *src*–Related Protein Tyrosine Kinases", *J Mol Evol* 42:247–256 (1996).

Inazu et al, "Purification and characterization of a novel dimeric 20 alpha–hydroxysteroid dehydrogenase from Tetrahymena pyriformis", *Biochem J* 297:195–200 (1994).

Kohn et al, "Expression of a Constitutively Active Akt Ser/Thr Kinase in 3T3–L1 Adipocytes Stimulates Glucose uptake and Glucose Transporter 4 Translcoation", *J. Biol. Chem* 271(49):31372–31378 (1996).

Lovri″ et al, "Activation of Mil/Raf protein kinases in mitotic cells", *Oncogene* 12:1109–1116 (1996).

Lange–Carter et al, "A Divergence in the MAP Kinase Regulatory Network Defined by MEK Kinase and Raf", *Science* 260:315–318 (1993).

Mason IJ, "The Ins and outs of Fibroblast Growth Factors", *Cell* 78:547–552 (1994).

McKenna et al, Atomic structure of the degraded procapsid particle of the bacteriophage G4: induced structural changes in the presence of calcium ions and functional implications. J. Mol. Biol. vol. 256, pp. 736–750(1996).

Mohammadi et al, "Structureo f the FGF Receptor Tyrosine Kinase Domain Reveals a Novel Autoinhibitory Mechanism", *Cell* 86:577–587 (1996).

Nishizuka Y, "Protein kinase C and lipid signaling for sustained cellular responses ", *FASEB J* 9:484–496 (1995).

Petit G, *Synthetic Peptides*, vol. 4., Amsterdam: Elsevier Sci. Pub. Co. pp 212, 223, 470 (1976).

Simmons et al, "Identification of an Early–Growth Response Gene Encoding a Novel Putative Protein Kinase", *Mol Cel Biol* 12:4164–4169 (1992).

Taylor et al, "cAMP–dependent protein kinase defines a family of enzymes", *Phil Trans R Soc Lond B* 340:315–324 (1993).

Kallunki et al, "JNK2 contains a specificity–determining region responsible for efficient c–Jun binding and phosphorylation", *Genes & Development* 8:2996–3007 (1994).

* cited by examiner a   untreated control b   Ara-c control c   SEQ ID NO: 2 d   SEQ ID NO: 3 e   SEQ ID NO: 22

Ara-c control     Ara-c +SEQ ID NO: 10

HJ-loop

```
TBR1       EIARRCSIGGI---HEDYQLPYYDLVPSDPSVEE
ACTR2      ELVSRCKAADG--PVDEYMLPFEEEIGQHPSLEE
BMR2       EIFMRCTDLFPGESVPEYQMAFQTEVGNHPTFED
TBR2       EMTSRCNAVGE---VKDYEPPFGSKVREHPCVES
ALK4       EIARRCNSGGV---HEEYQLPYYDLVPSDPSIEE
ALK3       EMARRCITGGI---VEEYQLPYYNMVPSDPSYED
ALK1       EIARRTIVNGI---VEDYRPPFYDVVPNDPSFED
           *:   *              :*   .:   :  ..*  *.
```

Alpha-D region
CLUSTAL X (1.81) multiple sequence alignment

```
TBR1       ----SDYHEHGSLFDYLNRYTVTVE
ACTR2      ----TAFHDKGSLTDYLKGNIITWNE
BMR2       ----MEYYPNGSLCKYLSLHTSDWV
TBR2           TAFHAKGNLQEYLTRHVISWE
ALK4       ----SDYHEHGSLFDYLNRYTVTIE
ALK3       ----TDYHENGSLYDFLKCATLDTR
ALK1       ----THYHEHGSLYDFLQRQTLEPH
               ::  :*.*  .:*
```

B4-B5 region

```
TBR1       ADNKDNG-TWTQLWLVSD
ACTR2      AEKRGSS-LEAELWLITA
BMR2       GDERVTADGRMEYLLVME
TBR2       AEERKTE-LGKQYWLITA
ALK4       ADNKDNG-TWTQLWLVSD
ALK3       ADIKGTG-SWTQLYLITD
ALK1       SDMTSRN-SSTQLWLITH
            .:            :  *:
```

A-region

```
TBR1       ----QTVMLRHENILGFIA
ACTR2      ----STPGMKHENLLQFIA
BMR2       ----RVPLMEHDNIARFIV
TBR2           SDINLKHENILQFLT
ALK4       ----QTVMLRHENILGFIA
ALK3       ----QTVLMRHENILGFIA
ALK1       ----NTVLLRHDNILGFIA
               :..*:*:   *:.. 
```

TISSUE REMODELING

CROSS-REFERENCE TO RELATED APPLICATIONS

The present application is a continuation-in-part of U.S. application Ser. No. 09/161,094, filed Sep. 25, 1998, now abandoned, and International Application PCT/US00/32852, filed Dec. 4, 2000, designating the United States, a Demand electing the United States having been timely filed on Jun. 13, 2001, the entire contents of both of which being hereby incorporated herein by reference.

FIELD OF THE INVENTION

The present invention concerns methods and compounds for changing (modulating) tissue-remodeling processes.

BACKGROUND OF THE INVENTION

The eukaryotic protein kinase superfamily is composed of enzymes which specifically phosphorylate serine, threonine or tyrosine residues of intracellular proteins. These enzymes are important in mediating signal transduction in multicellular organisms and are involved in a wide variety of cellular events. A few examples include: cellular proliferation, cellular differentiation, oncogenesis, immune responses, and inflammatory responses.

Enhanced protein kinase activity can lead to persistent stimulation by secreted growth factors and other growth inducing factors which, in turn, can lead to proliferative diseases such as cancer, to nonmalignant proliferative diseases such as arteriosclerosis, psoriasis and to inflammatory responses such as septic shock. Decreased function can also lead to disease. For example, a decrease in the activity of insulin receptor kinase is a cause of various types of diabetes.

Thus, agents which can modulate (increase or decrease) the activity of protein kinases have great potential for the treatment of a wide variety of diseases and conditions such as cancer, autoimmune disorders, and inflammation.

PKs are known to have homologous "catalytic domains" which are responsible to the phosphorylation activity. Based on a comparison of a large number of protein kinases, it is now known that the kinase domain of protein kinases can be divided into twelve subdomains. These are regions that are generally uninterrupted by large amino acid insertions and contain characteristic patterns of conserved residues (Hanks and Hunter, "The Eukaryotic Protein Kinase Superfamily", in Hardie and Hanks ed., The Protein Kinase Facts Book, Volume I, Academic Press, Chapter 2, 1995). These subdomains are referred to as Subdomain I through Subdomain XII.

Due to the high degree of homology found in the subdomains of different protein kinases, the amino acid sequences of the domains of different PKs can be aligned. Frequently, the alignment is carried out with reference to the prototypical protein kinase PKA-Cα, as known in the art. Currently, the catalytic domains of a large number of protein kinases have been aligned and tables showing these alignments are available from various published sources, such as, for example, in the article by Hanks and Quinn in Methods of Enzymology 200: 38–62 (1991) or in the PKR Web Site: www.sdsc.edu/kinases.

U.S. Pat. No. 6,174,993, International Application WO 98/53051 (corresponding to pending U.S. Application 08/861,153), International Application WO 00/118895 (corresponding to U.S. Ser. No. 09/161,094, now abandoned), U.S. applications Ser. No. 09/458,491, now abandoned (corresponding to WO 01/42280), and U.S. Ser. No. 09/734,520, now abandoned (corresponding to WO 02/48336) (all incorporated herein by reference) concern small, previously undisclosed, regions of various protein kinases with high substrate specificity. Short peptides derived from these regions were found to modulate kinase activities, as determined by the modulation of cellular activity in various in vivo and in vitro models. Without wishing to be bound by theory it is assumed that the short peptides disclosed in these applications, mimic some region of the catalytic domain of the kinase, bind to other cellular components with which the kinase interacts (such as the substrates of the kinase, other kinases, other phosphatases) and thus modulate kinase activity either by mimicking the kinase activity, or alternatively by inhibiting the interaction of the kinase and the cellular components thus inhibiting kinase-mediated signaling.

U.S. Pat. No. 6,174,993 and WO 98/53051 disclose a domain termed the HJ-loop. The "HJ-loop" referred to therein is found within the kinase domain of protein kinases between the middle of Subdomain IX and the middle of Subdomain X. Because of the high degree of homology found in the subdomains of different protein kinases, the amino acid sequences of the domains of different ser/thr protein kinases can be aligned. Thus, the HJ-loop of protein kinases can be defined by reference to the amino acid sequence of a prototypical protein kinase, for example PKA-Cα, and can be said to correspond to a contiguous sequence of about twenty amino acid residues found between about amino acid 229 and 248 of PKA-Cα.

A second definition of the HJ loop of protein kinases, which is complementary to the definition provided in the proceeding paragraph, can be made by reference to the secondary structure of the kinase domain of protein kinases. The kinase domain of protein kinases has been found to contain at least nine alpha helices, referred to as helix A through helix I, nine beta sheets, referred to as b1 through b9 (Tabor et al., Phil. Trans. R. Soc. Lond. B340: 315 (1993), Mohammadi et al., Cell 86:577 (1996) and Hubbard et al., Nature 372:746 (1994)). The HJ loop is a contiguous sequence of about twenty amino acids beginning within the F helix about five amino acids residues from the N-terminus of the F helix and extending about five amino acid residues into the G helix. It is noteworthy that the HJ-loop of the TGF-β/ILK family of protein kinases contains an insertion of about 12 to 15 extra amino acids as compared to other ser/thr or tyrosine (tyr) protein kinases.

WO 02/48336 discloses a region termed the "A-region". The "A-region" referred to herein is found within the kinase domain of PKs in Subdomain III and Subdomain IV. With respect to the amino acid sequence of the prototypical protein kinase PKA-Cα the A region can be said to correspond to a contiguous sequence of about eighteen amino acid residues found between about amino acids 92 and 109 of PKA-Cα. In some PKs, extra amino acids can be present in this region and the size of the A-region can, therefore, include more than 18 amino acids in length.

With respect to the secondary structure of protein kinases, the A region is a contiguous sequence of about five to twenty amino acids beginning at the middle of the αC helix (hereby αC) and ending at the beginning of the b4 beta sheet.

WO 01/42280 discloses a region termed B4–B5 region. The "B4–5 region" referred to herein is found within the kinase domain of PKs in Subdomain IV and the beginning of Subdomain V. With respect to the amino acid sequence of the prototypical protein kinase PKA-Cα, the B4–5 region can be said to correspond to a contiguous sequence representing the amino acid residues found between about amino acids 106 and 114 of PKA-Cα.

In some PKs, extra amino acids might be inserted in this region and the size of the B4–5 region can, therefore, include more than 9 amino acids in length.

A second definition of the B4–5 region of a PK, which is complementary to the definition provided in the preceding paragraph, can be made by reference to the three dimensional structure of the kinase domain of PKs. The kinase domain of PKs has been found to contain at least nine alpha helices, referred to as helix A through helix I and nine beta sheets, referred to as b1 through b9 (Tabor et al., *Phil. Trans. R. Soc. Lond.*, B340: 315 (1993), Mohammadi et al., *Cell*, 86:577 (1996) and Hubbard et al., *Nature* 372:746 (1994). The B4–5 region is a contiguous sequence of about five to twenty five amino acids beginning at the end of the b4 beta sheet and into the b5 beta sheet.

WO 00/18895 discloses a region termed the "αD region". The "αD region" referred to herein is found within the kinase domain of PKs in Subdomain V and the beginning of Subdomain VI. The "αD region" of a PK can be defined by reference to the amino acid sequence of a prototypical protein kinase, for example PKA-Cα and can be said to correspond to a contiguous sequence of about twenty amino acid residues found between about amino acid 120 and 139 of PKA-Cα.

In relation to the secondary structure of the kinase domain of PKs, the αD region is a contiguous sequence of about fifteen to forty amino acids beginning at the end of the b5 beta sheet and extending through the D helix and the following loop to the beginning of helix E.

The three dimensional structure of a number of kinases has been determined. A classical view of this structure is given in Knighton et al., *Science* 253, 407–414 (1991).

The superfamily of transforming growth factor beta (TGF-β), which include TGF-β, activins, and bone morphogenetic proteins (BMPs), are secreted agents that regulate a plurality of cellular responses such as proliferation, differentiation, migration and apoptosis.

TGF-β superfamily signaling has been implicated in a multitude of disorders and in various human diseases, including: cancer, fibrosis and autoimmune diseases. TGF-β superfamily members transduce their signals across the plasma membranes by inducing the formation of heteromeric complexes of specific type I and type II serine/threonine kinase receptors, which in turn activate a particular subset of SMAD proteins (some of them being inhibitory and some being excitatory). The SMAD molecule compounds relay the signals into the nucleus where they direct transcriptional responses in concert with other proteins.

TGF-β superfamily was found to be involved in embryogenesis-related physiological functions such as: regulation of growth, cell-faith specification, differentiation and apoptosis; in postnatal mechanisms including inhibition of cell growth (epithelial, vascular endothelial, hematopoietic cells and lymphocytes), induction of synthesis of IgA in B-lymphocytes, in control of wound healing processes and remodeling; in BMP-dependent responses including induction: of fibroblasts, osteoblasts in the process of cartilage and bone formation, respectively, involvement in bone genesis and spermatogenesis.

Malfunction connected with TGF-β has been linked to several clinical disorders including cancer, fibrosis, bone diseases, diabetic nephropathy, primary pulmonary hypertension, as well as chronic vascular diseases such as artheriosclerosis and hypertension.

There have been attempts to try and modify the process of bone healing by changing the concentrations of the TGF-β ligands. For example, various attempts have been made to increase the rate of bone healing by locally administrating to the fracture and of various TGF-β and BMP ligands, as well as by application of other growth factors. However, to date the results of these attempts have not been successful.

SUMMARY OF THE INVENTION

The present invention is based on the discovery that administration to the tissue of various compounds, which comprise peptides, having either a sequence appearing in one of four specific regions of TGF-β superfamily serine/threonine kinase receptor, or a variant of said sequence, resulted in a marked alteration of tissue remodeling processes in the tissue to which the compound was administered.

Without wishing to be bound by theory, it is assumed that the peptide part of the compound, mimics a region in the kinase that interacts with other cellular components such as the substrates of the kinase; phosphatases or other kinases which regulate the level of phosphorylation of the TGF-β kinase. The peptide part of the compound thus interrupts the interaction of the native kinase with the other cellular components (for example the substrates). Where the interaction between the kinase and the cellular component is an "on" reaction, i.e., having a net result of the increase of physiological property such as increased transcription (for example interaction of the TGF-β kinase with an excitatory SMAD), the effect of the interruption of the "on" reaction is inhibition of the property, for example inhibition of collagen synthesis. Where the interaction between the kinase and the cellular component is an "off" reaction, i.e., has a net result of decrease of physiological property, for example, decrease of transcription (such as interaction of TGFβ with inhibitory SMAD), the interruption of the "off" reaction results in increased physiological property such as increased transcription leading to increased bone healing.

Thus, the present invention concerns a method for the modulation of tissue-remodeling comprising: contacting the tissue to be remodeled with an effective amount of a compound comprising a sequence selected from:

(a) a sequence which is a continuous stretch of at least five amino acids present in a native TGF-β super family Ser/Thr kinase receptor, in positions of the receptor corresponding to positions 249 to 279 of TGF-βI receptor (HJ loop);

(b) a sequence which is a continuous stretch of at least five amino acids present in a native TGF-β super family Ser/Thr kinase receptor, in positions of the receptor corresponding to positions 119 to 139 of TGF-βI receptor (αD region);

(c) a sequence which is a continuous stretch of at least five amino acids present in a native TGF-β super family Ser/Thr kinase receptor, in positions of the receptor corresponding to positions 104 to 115 of TGF-βI receptor (B4–B5 region);

(d) a sequence which is a continuous stretch of at least five amino acids present in a native TGF-β super family Ser/Thr kinase receptor, in positions of the receptor corresponding to positions 89 to 103 of TGF-βI receptor (A-region);

(e) a variant of a sequence according to any one of (a) to (d) wherein up to 40% of the amino acid of the native sequence have been replaced with a naturally or non-naturally occurring amino acid or with a peptidomimetic organic moiety; and/or up to 40% of the amino acids have their side chains chemically modified; and/or up to 20% of the amino acids have been deleted; provided that at least 50% of the amino acids in the parent sequence of (a) to (d) are maintained unaltered in the variant, and provided that the variant maintains the biological activity of the parent sequences of (a) to (d);

(f) a sequence of any one of (a) to (e) wherein at least one of the amino acids is replaced by the corresponding D-amino acid;

(g) a sequence of any one of (a) to (f) wherein at least one of the peptidic backbones has been altered to a non-naturally occurring peptidic backbone;

(h) a sequence being the sequence of any one of (a) to (g) in reverse order; and (i) a combination of two o r more of the sequences of (a) to (h)

The term "tissue-remodeling", in the context of the present invention, refers to a wide variety of cellular and tissue-related processes which are characterized by a generation of new cells or tissues and/or degeneration of existing cells or tissues, or characterized by a change in the ratio between generation and degeneration of cells or extracellular matrix, which leads to a change in the entire tissue manifested by: increased tissue growth, decreased tissue growth, prevention of tissue formation, enhanced tissue healing, change in the proportion of various cell types in the tissue, change in the level of extracellular matrix in the tissue, etc. In particular, this term refers to, but is not limited to, bone remodeling (and in particular bone healing); skin-remodeling including in particular skin healing and prevention of scar formation in the skin; change of amount collagen deposition and in particular decrease of fibrosis formation, resulting in decreased scarring, and improved wound healing after surgery or injury, as well as decrease of post-surgery adhesions; change of cell proliferation and myogenic differentiation. This term includes, but is not limited to, skin remodeling, skin healing, scar formation, prevention of alopecia, improved hair growth, inhibition of fibrosis, modulation cell migration (including neuronal crest cell migration), modulating cell proliferation, modulating adipose tissue proliferation, and modulating myogenic differentiation.

The term "modulation" refers to a change (increase or decrease) in the level of tissue-remodeling, as compared to the level of tissue-remodeling in the absence of the compound of the invention or in the presence of a control compound. The change should be statistically significant. The change of level can be determined in accordance with each tissue remodeling phenomena, for example, modulation of bone healing (which is a tissue remodeling process) can be determined by decrease in the time required until complete bone healing, by measurement of the size of callous formation, by determination of the amount of the normal bone produced in a set period of time, etc. Modulation in connection with fibrosis may be carried out by comparing the size of fibrous tissue in a test as compared to control, by comparing the amount of collagen deposition in test vs. control, etc.

Modulation of an individual's tissue-remodeling refers to, for example, an inhibition of alopecia, enhancement of bone growth, prevention of fibrosis and scar formation, prevention of adipose cell proliferation, prevention of excess fibrosis formation in a plurality of diseases such as pulmonary fibrosis, chronic renal disease, scleroderma, liver cirrhosis, keloid formation, post-surgical adhesions and the like.

As will be explained later in detail, while direct assessment of tissue remodeling has to be carried out in tissue or in vivo, a good indication of tissue remodeling processes and modulation of said processes can be achieved by assessing the level of TGF-β-associated signal transduction in cells (for example by determination of TGF-β-dependent proliferation of fibroblasts) or in cell-free assays (such as by determination of the level of phosphorylation of the TGF-β-kinase substrates).

The term "compound (comprising sequence)" refers to a compound that includes therewithin any of the sequences of (a) to (i) as defined above. The compound may be composed mainly from amino acid residues, and in that case the amino acid component of the compound should comprise no more than a total of about 35 amino acids. Where the compound is mainly an amino acid compound, it may consist of any one of the amino acid sequences of (a) to (h), a combination of two or more, preferably of three most preferably of two, of the sequences of (a) to (h) linked to each other (either directly or via a spacer moiety) to give the combination of (i). The compound may further comprise any one of the amino acid sequences, or combinations as described above (in (a) to (i) above), together with additional amino acids or amino acid sequences. The additional amino acids may be sequences from other regions of the TGF-β-kinase, sequences that are present in the kinase vicinity of the regions, N-terminal or C-terminal to the sequences of (a) to (d), or sequences which are not present in the TGF-β-kinase but were included in the compound in order to improve various physiological properties, such as penetration into cells (sequences which enhance penetration through membranes or barriers); decrease degradation or clearance; decrease repulsion by various cellular pumps; improve immunogenic activities; improve various modes of administration (such as attachment of various sequences which allow penetration through various barriers, blood brain barrier, through the gut, etc.); increase specificity; increase affinity; decrease toxicity; and the like. A specific example is the addition of the amino acid Gly to the N-terminal of the sequence.

The compound may also comprise non-amino acid moieties, such as, for example, hydrophobic moieties (various linear, branched, cyclic, polycyclic or heterocyclic hydrocarbons and hydrocarbon derivatives) attached to the peptides of (a) to (i) to improve penetration, various protecting groups, especially where the compound is linear, attached to the compound's terminals to decrease degradation; chemical groups present in the compound to improve penetration or decrease toxic side effects; or various spacers, placed, for example, between one or more of the above amino acid sequences, so as to spatially position them in a suitable orientation in respect of each other. The compound of the invention may be linear or cyclic, and cyclization may take place by any means known in the art. Where the compound is composed predominantly of amino acids/amino acid sequences, cyclization may be N- to C-terminal, N-terminal to side chain and N-terminal to backbone, C-terminal to side chain, C-terminal to backbone, side chain to backbone and side chain to side chain, as well as backbone to backbone cyclization. Cyclization of the compound may also take place through the non-amino acid organic moieties.

The association between the amino acid sequence component of the compound and other components of the compound may be by covalent linking, by non-covalent complexion, for example, by complexion to a hydrophobic polymer, which can be degraded or cleaved producing a compound capable of sustained release; by entrapping the amino acid part of the compound in liposomes or micelles to produce the final compound of the invention. The association may be by the entrapment of the amino acid sequence within the other component (liposome, micelle) or the impregnation of the amino acid sequence within a polymer to give the final compound of the invention.

Preferably the compounds comprise an amino acid sequence of (a) to (i) above in association with (in the meaning described above) a moiety for transport across cellular membranes.

The term "moiety for transport across cellular membranes" refers to a chemical entity, or a composition of matter (comprising several entities) that causes the transport of members associated (see above) with it through phospholipidic membranes. One example of such moieties are hydrophobic moieties such as linear, branched, cyclic, polycyclic or heterocyclic substituted or non-substituted hydrocarbons. Another example of such a moiety are short peptides that cause transport of compounds attached to them into the cell by gradient derived, active, or facilitated transport. Other examples of other non-peptidic moieties known to be transported through membranes, such as glycosylated steroid derivatives, are well known in the art. Yet another example are moieties that are endocytosed by cellular receptors such as ligands of the EGF and tranferrin receptors. The moiety for the transport across membranes may be a polymer, liposome or micelle containing, entrapping or incorporating the amino acid sequence therein. In the above examples, the compound of the invention is the polymer, liposome, micelle, etc., impregnated with the amino acid sequence.

The term "a sequence which is a continuous stretch of at least 5 amino acids present . . . " refers to any continuous stretch of at least 5 amino acids, which are present in a longer amino acid sequence described by reference to positions of TGF-βI (see below). For example, if in a specific TGF-β Ser/Thr kinase receptor, the positions corresponding to amino acid residues X to Y of TGF-βI are amino acid residues 200 to 219 of that specific kinase, the continuous stretch of at least 5 amino acids may be from amino acid at position 200 to 204, from 201 to 205, from 216 to 220, from 210 to 214, etc. The continuous sequence may also be of 5, 6, 7, 8, 9, 10, 11, 12, 13, 14, 15, 16, 17, 18, 19 and 20 amino acids, obtained from each of these positions.

The term "TGF-β superfamily Ser/Thr kinase receptor" (hereinafter "TGF-β kinase") refers to both Type I receptors (ALK 1–7) as well as Type II receptors (ACTR-II, ACTR-IIb, TGF-B-II, BMPR-II, and AMHRII), and includes receptors which are activated by all of the ligands of the superfamily, examples of the ligands being TGF-β, BMP's, as activins/inhibins, AMH, and GDF. In one specific example, the TGF-β superfamily Ser/Thr kinase receptors are selected from ALK1, ALK2, ALK3, ALK4, ALK5, ALK6, TGF-B-II, activin RII, BMPRII and ILK.

The term "sequence corresponding to positions . . . to . . . of TGF-βI" refers to a sequence that matches the sequence appearing in the native TGF-βI receptor 1 when the sequence of the catalytic unit of the specific kinase is aligned with the sequence of the catalytic unit of TGF-βI. TGF-βI is identified as in the chain-D crystal structure of the cytoplasmic domain of TGF-β receptor in complex with Fkbp12 (gi 5542077 in the NCBI database, in the PDB entry). The positions of the TGF-βI receptor 1 kinase beginning in a certain position and ending in another position are indicated in the definition (a) to (d) above. For determining the beginning and end positions of the specific kinase used, the sequence of the catalytic unit of the specific kinase should be aligned with the sequence of the catalytic unit of TGF-βI in pair-wise or multiple alignment manner. Alignment may be carried out using any state of the art software such as ClustAl™ (version W or X).

FIG. 12 shows the alignment results of various kinases of the TGF superfamily Ser/Thr kinase receptor, in the above four regions, with TGF-βI. Of course where the kinase is TGFβ1 itself the positions are given, and there is no need for alignment.

The term "wherein up to 40% of amino acids of the native sequence have been replaced with a naturally or non-naturally occurring amino acid or with a peptidomimetic organic moiety" in accordance with the present invention, concerns an amino acid sequence, which shares at least 60% of its amino acid with the native sequence as described in (a), (b), (c) or (d) above, but some of the amino acids were replaced either by other naturally occurring amino acids, (both conservative and non-conservative substitutions), by non-naturally occurring amino acids (both conservative and non-conservative substitutions), or with organic moieties which serve either as true peptidomimetics (i.e., having the same steric and electrochemical properties as the replaced amino acid), or merely serve as spacers in lieu of an amino acid, so as to keep the spatial relations between the amino acid spanning this replaced amino acid. Guidelines for the determination of the replacements and substitutions are given in the detailed description part of the specification. Preferably no more than 30%, 25% or 20% of the amino acids are replaced.

The term "wherein up to 40% of the amino acids have their side chains chemically modified" refers to a variant which has the same type of amino acid residue, but to its side chain a functional group has been added. For example, the side chain may be phosphorylated, glycosylated, fatty acylated, acylated, iodinated or carboxyacylated. Other examples of chemical substitutions are known in the art and given below.

The term "up to 20% of the amino have been deleted" refer to an amino acid sequence which maintains at least 80% of its amino acids. Preferably no more than 10% of the amino acids are deleted and more preferably none of the amino acids are deleted.

The term "provided that at least 50% of the amino acids in the parent protein are maintained unaltered in the variants", the up to 40% substitution, up to 40% chemical modification and up to 20% deletions are combinatorial, i.e., the same variant may have substitutions, chemical modifications and deletions so long as at least 50% of the native amino acids are identical to those of the native sequence both as regards the amino acid and its position. In addition, the properties of the parent sequence, in modulating tissue remodeling (for example as determined by TGF-β associated signal transduction), have to be maintained in the variant, typically at the same or at a higher level.

When calculating 40% (or 35, 30, 25, 20%) replacements, or 20% (or 10%) deletions from sequences, the number of actual amino acids should be rounded mathematically, so that 40% of an 11-mer sequence (4.4) is four amino acids and 40% of a 12-mer sequence (4.8) is five amino acids.

Typically "essential amino acids" are maintained or replaced by conservative substitutions while non-essential amino acids may be maintained, deleted or replaced by conservative or non-conservative replacements. Generally, essential amino acids are determined by various Structure-Activity-Relationship (SAR) techniques (for example amino acids when replaced by Ala cause loss of activity) are replaced by conservative substitution while non-essential amino acids c an b e deleted or replaced by any type of substitution. Guidelines for the determination of the deletions, replacements and substitutions are given in the Detailed Description part of the specification.

The term "region" refers to a sequence in a specific location in the specific member of the TGF-β superfamily Ser/Thr kinase receptor which corresponds to the positions selected from: 249 to 279 of TGF-βI (termed: HJ loop); positions 119 to 139 (termed: αD loop); positions 104 to 115 (termed: B4–B5 region); and positions 89 to 103 (termed: A-loop).

The term "corresponding D-amino acid" refers to the replacement of the naturally occurring L-configuration of the natural amino acid residue by the D-configuration of the same residue.

The term "at least one peptidic backbone has been altered to a non-naturally occurring peptidic backbone" means that the bond between the N- of one amino acid residue to the C- of the next has been altered to non-naturally occurring bonds, for example, by reduction (to —$CH_2$—NH—), alkylation (methylation) on the nitrogen atom, or the bonds have been replaced by amidic bonds, urea bonds, or sulfonamide bonds, etheric bonds (—$CH_2$—O—), thioetheric bonds (—$CH_2$—S—), or to —CS—NH—. The side chain of the residue may be shifted to the backbone nitrogen to obtain N-alkylated-Gly (a peptidoid).

The term "in reverse order" refers to the fact that the sequence of (a) to (f) may have the order of the amino acids as it appears in the native TGF-β kinase from N- to the C-direction, or may have the reversed order (as read in the C- to N-direction). For example, if a subsequence of the A-region of TGFβ receptor is QTVML (residues 1–5 of SEQ ID NO:53) a sequence in a reverse order is LMVTQ (SEQ ID NO:60). It has been found that many times sequences having such a reverse order can have the same properties, in small peptides, as the "correct" order, probably due to the fact that the side chains, and not the peptidic backbones, are those responsible for interaction with other cellular components. Particularly preferred are what is termed "retro inverso" peptides—i.e., peptides that have both a reverse order as explained above, and in addition each and every single one of the amino acids has been replaced by the non-naturally occurring D-amino acid counterpart, so that the net end result, as regards the positioning of the side chains (the combination of reverse order and the change from L to D), is zero change. Such retro-inverso peptides, while having similar binding properties to the native peptide, were found to be resistant to degradation.

The present invention further concerns a method for the modulation of tissue-remodeling in a subject, comprising administering to a subject in need of such treatment a therapeutically effective amount of a compound comprising a sequence selected from:

(a) a sequence which is a continuous stretch of at least five amino acids present in a native TGF-β superfamily Ser/Thr kinase receptor, in positions of the kinase corresponding to positions 249 to 279 of TGF-β Receptor 1) (HJ loop);

(b) a sequence which is a continuous stretch of at least five amino acids present in a native TGF-β superfamily Ser/Thr kinase receptor, in positions of the kinase corresponding to positions 119 to 139of TGF-β Receptor 1 (αD region);

(c) a sequence which is a continuous stretch of at least five amino acids present in a native TGF-β superfamily Ser/Thr kinase receptor, in positions of the kinase corresponding to positions 104 to 115 of TGF-β Receptor 1 (B4–B5 region);

(d) a sequence which is a continuous stretch of at least five amino acids present in a native TGF-β superfamily Ser/Thr kinase receptor, in positions of the kinase corresponding to positions 89 to 103 of TGFβ TGF-β Receptor 1 (A-region);

(e) a variant of a sequence according to any one of (a) to (d) wherein up to 40% of the amino acid of the native sequence have been replaced with a naturally or non-naturally occurring amino acid or with a peptidomimetic organic moiety; and/or up to 40% of the amino acids have their side chains chemically modified; and/or up to 20% of the amino acids have been deleted; provided that at least 50% of the amino acids in the parent sequence of (a) to (d) are maintained unaltered in the variant, and provided that the variant maintains the biological activity of the parent sequences of (a) to (d);

(f) a sequence of any one of (a) to (e) wherein at least one of the amino acids is replaced by the corresponding D-amino acid;

(g) a sequence of any one of (a) to (f) wherein at least one of the peptidic backbones has been altered to a non-naturally occurring peptidic backbone;

(h) a sequence being the sequence of any one of (a) to (g) in reverse order; and (i) a combination of two or more of the sequences of (a) to (h).

The term "subject" in the meaning of the present invention concerns a human, but can also include animals for veterinary purposes.

The term "therapeutically effective amount" is the quantity of compound which results in an improved clinical outcome as a result of the treatment compared with a typical clinical outcome in the absence of the treatment. An "improved clinical outcome" results in an individual with the disease experiencing fewer symptoms or complications of the disease, including a longer life expectancy, as a result of the treatment as well as the prevention of the disease before it occurs. With respect to bones, an "improved clinical outcome" includes, but is not limited, to a shorter time period until bone healing is achieved; or to the healing of bone in cases where normal bone healing does not take place such as where a large bone section is missing ("non-union"). With respect to post-surgical fibrosis or scarring, the term refers to smaller amount fibrosis or scarring or prevention of the formation of either one before they are expected to occur, such as prevention of scarring or fibrosis after surgery. With respect to alopecia it concerns elimination or decrease in the amount of hair-loss in general and in particular following chemotherapeutic or radiotherapeutic treatment. The amount of compounds of the invention administered to the individual will depend on the type and severity of the disease and on the characteristics of the individual, such as general health, age, sex, body weight and tolerance to drugs as well as on the mode of administration. In the case of tissue remodeling, many applications are local to the tissue, the amounts used when locally administered may be smaller than in systemic administration. The skilled artisan will be able to determine appropriate dosages depending on these and other factors. Typically, a therapeutically effective amount of the compound can range from about 1 mg per day to about 1000 mg per day for an adult. Preferably, the dosage ranges from about 1 mg per day to about 100 mg per day.

The method for therapeutic treatment, by way of tissue remodeling may be used for improving bone healing (including improvement in rate of healing, achievement of healing in cases where a large bone segment "non-union" is missing, augmentation of various bones, increasing the probability of obtaining healthy bones); decreasing fibrosis (as determined by decreased scarring, decreased adhesion, decreased deposition of collagen and extracellular matrix in various diseases and post-operational and injury including injury to the skin and connective tissue), decreased alopecia and the like.

The present invention also concerns methods for obtaining the above compounds which can be used in a method for modulation of tissue remodeling. Thus the present invention concerns a method for obtaining a compound for the modulation of tissue-remodeling the method comprising:

(i) providing a plurality of candidate compounds comprising the sequences as defined above;

(ii) assaying the candidate compounds obtained in (i) in a test assay and determining the level of tissue-remodeling;

(iii) selecting those compounds which modulate tissue-remodeling as compared to the tissue-remodeling in the same test assay in the absence of the candidate compounds, thereby obtaining compounds being capable of modulating tissue modulating activities.

Assays for determining tissue-modeling activity will be specified in more detail hereinafter below. However, many of these assays require testing in vivo, or in tissue cultures, and thus are rather expensive and complicated for initial screening purposes. Therefore, many times it is preferable to conduct initial screening in a cellular, or cell-free system, which is used to determine the level of TGF-β superfamily Ser/Thr kinase receptor signal transduction pathways. Examples of such systems are assays for determination of the number of cells, which proliferation is dependent on this pathway, measurement of collagen deposition by cells, determination of level of phosphorylation of the substrate of the TGF-β kinase in intact cells or in cell free systems and the like. Compounds which are capable of modulating a TGF-β associated signal transduction have a high probably of also being active in tissue remodeling, however, this activity still has to be verified in a more relevant physiological assays.

Typically, modulation of the level of TGF-β associated signal transduction refers to a change in the level of phosphorylation of at least one the TGF-β substrate (which may be the direct or indirect substrate.

It should be appreciated that for the purpose of modulation, it is best to choose a compound comprising sequences derived from the same member of the TGF-β superfamily Ser/Thr kinase receptor as the one known (for example, in literature or from clinical information) to be involved in the modulation of the specific tissue of interest.

It should be appreciated that some of compounds comprising the sequences of (a) to (i) above, have better tissue remodeling modulating activities than others, and the selection of the compounds which are active in the tissue remodeling process should be done according to the method as indicated above.

Preferably, the determination of the sequence to be included in the candidate compound for modulating tissue remodeling should be carried out with the following steps:

(i) determining which specific member of the TGF-β superfamily Ser/Thr kinase receptor is involved in the remodeling of the tissue to be modulated, and determining the sequence of the specific member from a database of amino acid sequences;

(ii) aligning the sequence of the catalytic unit of the member obtained in (i) with the sequence of the catalytic unit of TGF-βI receptor, and determining the sequence of the specific member in four regions corresponding, in the alignment, to the following, positions of TGF-βI: 249 to 279 (HJ-loop), 119 to 139(αD region), 104 to 115 (B4–B5 region), 89 to 103 (A-region);

(iii) determining a continuous stretch of at least 5 amino acids of any of the four regions of (ii) above, that is sorter than the length of the entire region and has modeling activities of the tissue-remodeling or TGF-βkinase associated signal transduction, by: synthesizing a plurality of subsequences (optionally partially overlapping subsequences) of 5–10 mer from any of the above four regions; testing those sequences in a test assay for determining tissue-remodeling or TGF-β-associated signal transduction modulating activities, and selecting those sequences that have tissue remodeling or TGF-β-associated signal transduction modulating activities;

(iv) determining in the sequences of (ii) or in the sequences selected in (iii) above, essential and non-essential amino acids by: preparing a plurality of modified sequences wherein in each modified sequence a single and different position in the native sequence has been replaced with a test amino acid (preferably with Ala); testing those modified sequences in a test assay to determine tissue-remodeling or TGF-β-associated signal transduction modulating activities; those amino acids which when replaced caused a statistically significant change in tissue-remodeling TGF-β-associated signal transduction modulating activity being essential amino acids, and those amino acids which when replaced, did not cause a statistically significant change in tissue remodeling/TGF-β-associated signal transduction modulating activity, being non-essential amino acids;

(v) preparing a plurality of compounds comprising sequences selected from:
(1) the sequences of (ii);
(2) the sequences selected in (iii);
(3) the sequences of (ii) or the selected sequence of (iii), wherein at least one of the essential amino acids has been replaced by a conservatively substituted naturally or non-naturally occurring amino acid, or a conservative peptidomimetic organic moiety; and/or at least one of the non-essential amino acids has been deleted, or substituted (conservatively or non-conservatively) by naturally or non-naturally occurring amino acids or a peptidomimetic;
(4) the sequences of (1) to (3) in a reverse order;
(5) the sequence of (4) wherein all the amino acids have been replaced by their D-counterpart residues;

said compounds of (v) being candidate compounds for modulating tissue remodeling.

Conceptually, the first step is deciding which specific member of the TGF-β superfamily Ser/Thr kinase receptor is involved in the tissue-remodeling which is to be modulated. This can be done for example by carrying out a literature search, and determining which kinase is known to be involved in the processes of tissue remodeling that is to be modulated.

Once this specific kinase is identified, its sequence can be obtained from amino acid sequence databases and it is possible to locate the above four regions, simply by aligning the sequence of the catalytic unit of the specific kinase chosen, as present in the database, with the TGF-β Receptor I catalytic subunit, and by this finding the specific sequences of the four regions. Although the sequences of the region are not very long (12–31 amino acids long), it is of course desirable to find the shorter subsequence of at least 5 continuous amino acids present within this full region, and use this shorter sequence in the compound of the invention. Finding this short subsequence is a routine procedure, which can be achieved by several possible manners, such as by synthesizing sequences of 5–10 mer having partially overlapping, or adjacent sequences, and optionally optimizing the chosen sequence (if rather longer sequences such as, for example, 8–10 mer are used) by sequentially deleting from one or both of its terminal amino acids until the optimal shorter sequence (not necessarily the shortest but a combination of length and activity should be considered) sequence still having tissue-remodeling modulating activities is obtained.

After obtaining shorter subsequence which still has tissue-remodeling properties (as may be determined both by a tissue-remodeling assay or in an indicative assay such as modulation of TGF-β-kinase associated signal transduction), it is necessary to find which amino acids either in the sequence of the full region but preferably in the sequence of the shorter subsequence are essential (crucial for the modulating activity) and which are non-essential. This can be done by routine procedure, wherein a plurality of sequences are prepared, wherein in each sequence a single (and different) amino acid has been replaced, as compared to the native sequence by a "test amino acids"— usually the amino acid residue Alanine (a procedure known as: "Ala-scan"). Each of the plurality of sequences is again tested for its tissue-remodeling/TGF-β-associated signal transduction modulating activities. Amino acids which when replaced cause lost, or substantial decrease in the modulating activity of the full sequence is considered as "essential amino acids". Amino acids which when replaced do not caused a change of modulating activity of the sequence are referred to as "non-essential" amino acids (the loss or decrease should be determined by statistically significant manners).

Finally, as a last step, a plurality of sequences is prepared which may comprise either the full native sequence of any of the regions, short subsequence of at least 5 amino acids as appearing in any of the regions, sequences wherein at least one essential amino acid has been replaced by conservative substitution by a naturally, non-naturally occurring amino acid or by a peptidomimetic organic moiety; and/or an amino acid sequence wherein at least one amino acid (present in a non-essential position) has been deleted, or an amino acid in a non-essential position has been replaced by conservative or non-conservative substitution by a naturally occurring, non-naturally occurring, or organic peptidomimetic moiety.

For example, 1, 2, 3, 4, 5, 6, 7, 8, amino acids may be replaced in the sequence used in the compound of the invention as compared with the native sequence present in the kinase. The total combination of replacements, deletions, etc. should be such that the resulting variant host where at least 50% of the amino acids of the native sequence are present unaltered.

A notable exception to the above is the use of retro-inverso amino acids (in reverse order as compared to the native sequence), where when the peptide is in the reversed order, all of its amino acids are replaced with their D-counterparts.

When preparing the compound, it is possible to proceed by one of two strategies: by one strategy it is possible to test (for tissue remodeling or TGF-β-associated signal transduction modulating activities) a full compound—i.e., a compound comprising both a candidate sequence, and for example, non-amino acid moieties such as hydrophobic moieties present in one of its terminals. This strategy is generally used where the test assay is intact cells or in-vivo where the issue of penetration through membranes, addressed by addition of a hydrophobic moiety, is crucial.

Alternatively, it is possible to first optimize the sequence alone (preferably by testing it in a cell-free system for TGF-β-signaling dependent phosphorylation) so as to first find the best sequence possible, and then add to the optimal sequence other moieties, such as hydrophobic moieties, etc. to improve other properties of the compound as a whole such as for improving the penetration into cells, resistance to degradation, etc.

The present invention also concerns compounds for modulation of tissue-remodeling obtained by any of the above methods.

The present invention further concerns pharmaceutical compositions comprising the above compounds as active ingredients. The pharmaceutical composition may contain one species of compounds of the invention or a combination of several species of the invention.

The pharmaceutical compositions of the invention should be used for treatment of conditions or disorders wherein a therapeutically beneficial effect can be evident through the modulation of tissue remodeling.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 12 shows multiple alignment of several members of the TGF-β superfamily Ser/Thr kinase receptors with TGF-β Receptor I in the four regions; HJ loop (SEQ ID NOs:32–38), αD-region (SEQ ID NOs:39–45), B4–B5 region (SEQ ID NOs:46–52) and A-region (SEQ ID NOs:53–59).

DETAILED DESCRIPTION OF THE INVENTION

Figure 1:
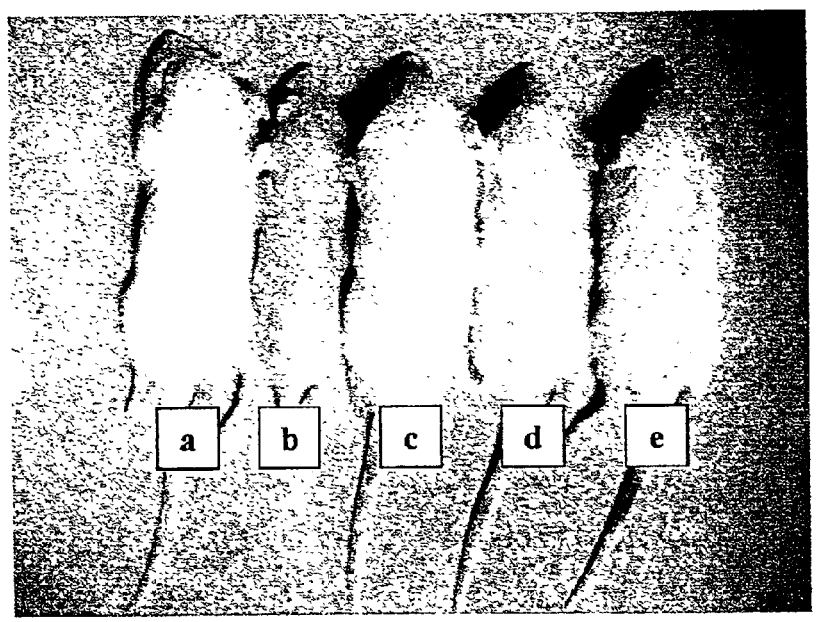
FIG. 1 illustrates the inhibition of chemotherapy-induced alopecia by a compound comprising ALK (activin-like kinase) peptide/peptide variant, (K048H101 and K098H901).

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the intention.

1. Addition of Non-peptidic Groups to Produce the Compound of the Invention

Where the compound of the invention is linear, it is possible to place in any of its terminal various functional groups. The purpose of such a functional group may be for the improvement of the tissue-remodeling modulating activities. The functional groups may also serve for the purpose of improving physiological properties of the compound not related directly to tissue-remodeling modulation properties such as: improvement in stability, penetration, tissue localization, efficacy, decrease of clearance, decrease toxicity, improved selectivity, improved resistance to repletion by cellular pumps, penetration through barrier (blood, brain, gut) and the like. For convenience sake the free N-terminal of one of the sequences contained in the compounds of the invention will be termed as the N-terminal of the compound, and the free C-terminal of the sequence will be considered as the C-terminal of the compound (these terms being used for convenience sake). Either the C-terminus or the N-terminus of the sequences, or both, can be linked to a carboxylic acid functional group or an amine functional group, respectively.

Suitable functional groups are-described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound comprising into a cell, for example, by reducing the hydrophilicity and increasing the lipophilicity of the compound.

These moieties can be cleaved in vivo, either by hydrolysis or enzymatically, inside the cell. (Ditter et al., *J. Pharm. Sci.* 57:783 (1968); Ditter et al., *J. Pharm. Sci.* 57:828 (1968); Ditter et al., *J. Pharm. Sci.* 58:557 (1969); King et al., *Biochemistry* 26:2294 (1987); Lindberg et al., *Drug Metabolism and Disposition* 17:311 (1989); and Tunek et al., *Biochem. Pharm.* 37:3867 (1988), Anderson et al., *Arch. Biochem. Biophys.* 239:538 (1985) and Singhal et al., *FASEB J.* 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a compound of the present invention is protected, preferably with a methyl, ethyl, benzyl or substituted benzyl ester, more preferably as a benzyl ester.

In addition, a modified lysine residue can be added to the C-terminal of the compound to enhance biological activity. Examples of lysine modification include the addition of an aromatic substitute, such as benzoyl benzoic acid, dansyl-lysine various derivatives of benzoic acids (difluoro-, trifluoromethy-, acetamido-, dimethyl-, dimethylamino-, methoxy-) or various derivatives of carboxylic acid (pyrazine-, thiophene-, pyridine-, indole-, naphthalene-, biphenyl,), or an aliphatic group, such as acyl, or a myristic or stearic acid, at the epsilon amino group of the lysine residue.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include $CH_3$—O—CO—, (ethyl)—O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Other examples of N-terminal protecting group includes adamantane, naphthalene, myristoleyl, toluene, biphenyl, cinnamoyl, nitrobenzoyl, toluoyl, furoyl, benzoyl, cyclohexane, norbornane, and Z-caproic. In order to facilitate the N-acylation, one to four glycine residues can be present in the N-terminus of the compound.

The carboxyl group at the C-terminus of the compound can be protected, for example, by an amide (i.e., the hydroxyl group at the C-terminus is replaced with —$NH_2$, —$NHR_2$ and —$NR_2R_3$) or ester (i.e., the hydroxyl group at the C-terminus is replaced with —$OR_2$). $R_2$ and $R_3$ are independently an aliphatic, substituted aliphatic, benzyl, substituted benzyl, aryl or a substituted aryl group. In addition, taken together with the nitrogen atom, $R_2$ and $R_3$ can form a $C_4$ to $C_8$ heterocyclic ring with from about 0–2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$—NH(ethyl), —N(ethyl)$_2$, —N(methyl) (ethyl), —NH(benzyl), —N(C1–C4 alkyl) (benzyl), —NH(phenyl), —N(C1–C4 alkyl) (phenyl), —$OCH_3$, —O—(ethyl), —O—(n-propyl), —O—(n-butyl), —O—(iso-propyl), —O—(sec-butyl), —O—(t-butyl), —O—benzyl and —O—phenyl.

Preferably the compound includes in the N-terminal a hydrocarbon having a length of $C_4$–$C_{20}$ preferably $C_6$–$C_{18}$, Most preferably $Cl_{10}$–$C_{16}$. Example of hydrophobic moieties are: myristoyl, stearyl, lauroyl, palmitoyl and acetyl etc.

2. Finding the Shortest Continuous Stretch-subsequence of the Region

As indicated, the sequence from which the continuous stretch of amino acids is chosen is identified by aligning the amino acid of the catalytic unit of a specific member of the TGF-β superfamily Ser/Thr kinase receptor, involved in the specific tissue-remodeling with the catalytic unit of TGF-βI and determining the positions corresponding to 249 to 279 (HJ loop), 119 to 139 (αD), 104 to 115 (B4–B5 region) and 89 to 103 (A-region). The positions define a region of about 12–31 aa.

The continuous stretch of at least five can be found by preparing a series of partially overlapping peptides each of 5–10 amino acids and each obtained by synthesizing a sequence that is one position removed from the previous sequence.

For example, if the HJ region of a specific member is in position 249–279, and it is to be desired to prepare 10 mer peptides, then the following, partially overlapping peptides are prepared, a peptide having the sequence 249–258, 250–259, 251–260, 252–261 . . . 270–279. The tissue-remodeling modulating activity is then determined in an assay which is relevant to the tissue to be remodeled. The best 10-mer peptide is then chosen.

For checking whether the 10 mer peptide can be reduced in sequence, it is possible to either repeat the above procedure (preparing a series of partially overlapping peptides) using 5 mer peptides that span the length of the 10 mer peptide, or to shorten the 10 mer peptide by deleting alternatively from each terminal an amino acid and testing the tissue remodeling modulating activity of the progressively truncated peptides, until the optimal sequence of at least 5, at least 6, at least 7, at least 8, at least 9 mer peptide is obtained, or determining whether longer sequences are required. As the regions are relatively small, the number of different peptides to be tested is also small. For example, for a region αD having a length of about 20 aa, there is a need to prepare only 12 peptides to find the optimal 8 mer peptide. After the best 8-mer peptide is obtained, it is possible to delete sequentially amino acids from one or both terminals of the 8 mer peptide for obtaining the shortest sequence of 5, 6 or 7 mer that is still active. For these steps only 16 sequences have to be tested.

3. Identifying Essential and Non-essential Amino Acids in the Subsequence Chosen A. Ala-Scan Once the shorter continuous stretch of at least 5 (at least 6, 7, 8, 9, 10, 11 or 12) amino acids has been identified, as explained above, it is necessary to realize which of the amino acids in the stretch are essential (i.e. crucial for the tissue remodeling or to the TGF-β-associated signal transduction modulating activity) and which are non-essential. Without wishing to be bound by theory, in almost every native protein involved in interaction with other cellular components, some amino acids are involved with the interaction (essential amino acids) and some amino acids are not involved in the interaction (non-essential amino acids), for example since they are cryptic. A short peptide which is to mimic a region of the TGF-β-kinase protein behaves in the same way as the region when present in the full kinase: some amino acids actually interact with the substrate (or other interacting cellular components) and other amino acids merely serve to spatially position the interacting amino acids, but do not participate in the interaction with the other cellular components.

Essential amino acids have to be maintained (i.e., be identical to those appearing in the native kinase), or replaced by conservative substitutions (see definition below) to obtain variants of the peptides. Non-essential amino acids can be maintained, deleted, replaced by a spacer or replaced by conservative or non-conservative substitutions.

Identification of essential vs. non-essential amino acids in the peptide can be achieved by preparing several peptides that have a shorter sequence than the full region (see Example 2 above) in which each amino acid is sequentially replaced by the amino acid Ala ("Ala-Scan."), or sequentially each amino acid is omitted ("omission-scan"). This allows to identify the amino acids which modulating activity is decreased by said replacement/omission ("essential") and which are not decreased by said replacement/omission ("non-essential") (Morrison et al., *Chemical Biology* 5:302–307, 2001). Another option for testing the importance of various peptides is by the use of site-directed mutagenesis. Other Structure-Activity-Relationship techniques may also be used.

B. 3D-analysis

Another strategy for finding essential vs. non-essential amino acids is by determining which aa of the A-region, in the 3D of the full kinase are exposed and which are cryptic. This can be done using standard software such as SPDB viewer, "color by accessibility" of Glaxo-Welcome.

Typically cryptic aa are non-essential and exposed or partially exposed amino acids are more likely to be essential. However, if one wishes to "guess" theoretically which "non-conservative" substitutions in the cryptic region can be tolerated, a good guideline is to "check" on a 3D computer model of the full kinase, whether a peptide superimposed on the full kinase and bearing those changes has still the overall structure of the region and more importantly, whether the exposed amino acids in the variants still overlap the positions of the exposed amino acids in the full kinase. Those non-conservative substitution, that when simulated on a computer 3D structure (for example using the Tripose™ software) do not cause drastic alteration of the overall shape of the region (drastic shifting in the position of the exposed aa) are likely non-conservative replacements. Thus prior to experimental testing it is possible to reduce the number of tested candidates by computer simulation. Where the 3D structure of a specific kinase is not available in activating crystallography data, it is possible to obtain a "virtual" 3D structure of the kinase based on homology to known crystallographic structures using such progress such as CompSer™ (Tripose, USA).

4. Obtaining Variants

The sequence regions of the compound of the invention may be the native sequences obtained from the TGF-β-kinase (preferably the shortest possible sequence from the regions), or alternatively variants of the native sequence obtained by deletion, (of non-essential amino acids) or substitution (only conservative substitutions in essential positions, both conservative and non-conservative of non-essential acids), or of chemical modifications.

4.1 Deletions and Insertions

Deletions can occur in particular of the "non-essential amino acids". Additions may occur in particular at the N-terminal or the C-terminal of any of the amino acids of the sequence. No more than 20%, preferably 10% most preferably none of the amino acids should be deleted. Insertions should preferably be N-terminal or C-terminal to the sequence of (a) to (h) or between the several sequences linked to each other in (i). However other insertions or deletions are possible. Again, the feasibility of the deletions in creating a peptide which is a good mimic can be evaluated virtually by reverting to the 3D-modeling as described above, and finding which deletions still maintain the exposed side chains in the same orientation (when the peptide is superimposed virtually on the kinase in the same positions so as to determine whether deletions change drastically spatial orientation of the exposed side chains.

4.2 Replacements

The variants can be obtained by replacement (termed also in the text as "substitution") of any of the amino acids as present in the native kinase. As may be appreciated there are positions in the sequence that are more tolerant to substitutions than others, and in fact some substitutions may improve the activity of the native sequence. The determination of the positions may be realized using "Ala-Scan," "omission scan" "site directed mutagenesis" or 3-D theoretical considerations as described in 3 above. Generally speaking the amino acids which were found to be "essential" should either be identical to the amino acids present in the native specific kinase or alternatively substituted by "conservative substitutions" (see bellow). The amino acids which were found to be "non-essential" might be identical to those in the native peptide, may be substituted by conservative or non-conservative substitutions, and may be deleted or replaced by a "spacers".

The term "naturally occurring amino acid" refers to a moiety found within a peptide and is represented by —NH—CHR—CO—, wherein R is the side chain of a naturally occurring amino acid.

The term "non-naturally occurring amino acid" (amino acid analog) is either a peptidomimetic, or is a D or L residue having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. This term also refers to the D-amino acid counterpart of naturally occurring amino acids. Amino acid analogs are well-known in the art; a large number of these analogs are commercially available. Many times the use of non-naturally occurring amino acids in the peptide has the advantage that the peptide is more resistant to degradation by enzymes which fail to recognize them.

The term "conservative substitution" in the context of the present invention refers to the replacement of an amino acid present in the native sequence in the specific kinase with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid). However where the native amino acid to be replaced is charged, the conservative substitution according to the definition of the invention may be with a naturally occurring amino acid, a non-naturally occurring amino acid or a peptidomimetic moiety which are charged, or with non-charged (polar, hydrophobic) amino acids that have the same steric properties as the side-chains of the replaced amino acids. The purpose of such a procedure of maintaining the steric properties but decreasing the charge is to decrease the total charge of the compound.

For example in accordance with the invention the following substitutions are considered as conservative: replacement of arginine by citrulline; arginine by glutamine; aspartate by asparagine; glutamate by glutamine.

As the naturally occurring amino acids are grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The following are some non-limiting examples of groups of naturally occurring amino acids or of amino acid analogs are listed bellow. Replacement of one member in the group by another member of the group will be considered herein as conservative substitutions:

Group I includes leucine, isoleucine, valine, methionine, phenylalanine, serine, cysteine, threonine and modified amino acids having the following side chains: ethyl, n-butyl, —$CH_2CH_2OH$, —$CH_2CH_2CH_2OH$, —$CH_2CHOHCH_3$ and —$CH_2SCH_3$. Preferably Group I includes leucine, isoleucine, valine and methionine.

Group II includes glycine, alanine, valine, serine, cysteine, threonine and a modified amino acid having an ethyl side chain. Preferably Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamine, asparagine, CO—NH-alkylated glutamine or asparagine (e.g., methyl, ethyl, n-propyl and iso-propyl) and modified amino acids having the side chain —$(CH_2)_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, glutamine, asparagine, methyl aspartate, ethyl aspartate, benzyl aspartate and methyl glutamate, ethyl glutamate and benzyl glutamate.

Group V includes histidine, lysine, arginine, N-nitroarginine, β-cycloarginine, μ-hydroxyarginine, N-amidinocitruline and 2-amino-4-guanidinobutanoic acid, homologs of lysine, homologs of arginine and ornithine. Preferably, Group V includes histidine, lysine, arginine, and ornithine. A homolog of an amino acid includes from 1 to about 3 additional methylene units in the side chain.

Group VI includes serine, threonine, cysteine and modified amino acids having C1–C5 straight or branched alkyl side chains substituted with —OH or —SH. Preferably, Group VI includes serine, cysteine or threonine.

In this invention any cysteine in the original sequence or subsequence can be replaced by a homocysteine or other sulfhydryl-containing amino acid residue or analog. Such analogs include lysine or beta amino alanine, to which a cysteine residue is attached through the secondary amine yielding lysine-epsilon amino cysteine or alanine-beta amino cysteine, respectively.

The term "non-conservative substitutions" concerns replacement of the amino acid as present in the native TGF-kinase by another naturally or non-naturally occurring amino acid, having different electrochemical and/or steric properties, for example as determined by the fact the replacing amino acid is not in the same group as the replaced amino acid of the native kinase sequence. Those non-conservative substitutions which fall under the scope of the present invention are those which still constitute a compound having kinase-associated signal transduction modulating activities. Because D-amino acids have hydrogen at a position identical to the glycine hydrogen side-chain, D-amino acids or their analogs can often be substituted for glycine residues, and are a preferred non-conservative substitution.

A "non-conservative substitution" is a substitution in which the substituting amino acid (naturally occurring or modified) has significantly different size, configuration and/or electronic properties compared with the amino acid being substituted. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—CH$_2$)$_5$COOH]—CO— for aspartic acid.

Alternatively, a functional group may be added to the side chain, deleted from the side chain or exchanged with another functional group. Examples of non-conservative substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. In yet another alternative, the side chain of the substituting amino acid can have significantly different steric and electronic properties from the functional group of the amino acid being substituted. Examples of such modifications include tryptophan for glycine, lysine for aspartic acid and —(CH$_2$)$_4$COOH for the side chain of serine. These examples are not meant to be limiting.

As indicated above the non-conservative substitutions should be of the "non-essential" amino acids.

Preferably, the TGFβ-kinase may be substituted by benzylamine groups, by biotinylation. Another substitution is di-iodinization of tyrosine. Liposomes may be substituted by D-isomers especially D-Lys residues.

"Peptidomimetic organic moiety" can be substituted for amino acid residues in the compounds of this invention both as conservative and as non-conservative substitutions. These peptidomimetic organic moieties either replace amino acid residues of essential and non-essential amino acids or act as spacer groups within the peptides in lieu of deleted amino acids (of non-essential amino acids). The peptidomimetic organic moieties often have steric, electronic or configurational properties similar to the replaced amino acid and such peptidomimetics are used to replace amino acids in the essential positions, and are considered conservative substitutions. However such similarities are not necessarily required. The only restriction on the use of peptidomimetics is that the compounds retain their tissue-remodeling modulating activity as compared to compounds constituting sequence regions identical to those appearing in the native kinase.

Peptidomimetics are often used to inhibit degradation of the peptides by enzymatic or other degradative processes. The peptidomimetics can be produced by organic synthetic techniques. Examples of suitable peptidomimetics include D amino acids of the corresponding L amino acids, tetrazol (Zabrocki et al., *J. Am. Chem. Soc.* 110:5875–5880 (1988)); isosteres of amide bonds (Jones et al., *Tetrahedron Lett.* 29: 3853–3856 (1988));

LL-3-amino-2-propenidone-6-carboxylic acid (LL-Acp) (Kemp et al., *J. Org. Chem.* 50:5834–5838 (1985)). Similar analogs are shown in Kemp et al., *Tetrahedron Lett.* 29:5081–5082 (1988) as well as Kemp et al., *Tetrahedron Lett.* 29:5057–5060 (1988), Kemp et al., *Tetrahedron Lett.* 29:4935–4938 (1988) and Kemp et al., *J. Org. Chem.* 54:109–115 (1987). Other suitable peptidomimetics are shown in Nagai and Sato, *Tetrahedron Lett.* 26:647–650 (1985); Di Maio et al., *J. Chem. Soc. Perkin Trans.*, 1687 (1985); Kahn et al., *Tetrahedron Lett.* 30:2317 (1989); Olson et al., *J. Am. Chem. Soc.* 112:323–333 (1990); Garvey et al., *J. Org. Chem.* 56:436 (1990). Further suitable peptidomimetics include hydroxy-1,2,3,4-tetrahydroisoquinoline-3-carboxylate (Miyake et al., *J. Takeda Res. Labs* 43:53–76 (1989)); 1,2,3,4-tetrahydro-isoquinoline-3-carboxylate (Kazmierski et al., *J. Am. Chem. Soc.* 133:2275–2283 (1991)); histidine isoquinolone carboxylic acid (HIC) (Zechel et al., *Int. J. Pep. Protein Res.* 43 (1991)); (2S, 3S)-methyl-phenylalanine, (2S, 3R)-methyl-phenylalanine, (2R, 3S)-methyl-phenylalanine and (2R, 3R)-methyl-phenylalanine (Kazmierski and Hruby, *Tetrahedron Lett.* (1991)).

4.3 Chemical Modifications

In the present invention the side amino acid residues appearing in the native sequence may be chemically modified, i.e. changed by addition of functional groups. The modification may be in the process of synthesis of the compound, i.e. during elongation of the amino acid chain and amino acid, i.e. a chemically modified amino acid is added. However, chemical modification of an amino acid when it is present in the compound or sequence ("in situ" modification) is also possible.

The amino acid of any of the sequence regions of the compound can be modified (in the peptide conceptionally viewed as "chemically modified") by carboxymethylation, acylation, phosphorylation, glycosylation or fatty acylation. Ether bonds can be used to join the serine or threonine hydroxyl to the hydroxyl of a sugar. Amide bonds can be used to join the glutamate or aspartate carboxyl groups to an amino group on a sugar (Garg and Jeanloz, Advances in *Carbohydrate Chemistry and Biochemistry*, Vol. 43, Academic Press (1985); Kunz, Ang. Chem. int. Ed. English 26:294–308 (1987)). Acetal and ketal bonds can also be formed between amino acids and carbohydrates. Fatty acid acyl derivatives can be made, for example, by free amino group (e.g., lysine) acylation (Toth et al., Peptides: *Chemistry, Structure and Biology*, Rivier and Marshal, eds., ESCOM Publ., Leiden, 1078–1079 (1990)).

4.4 Cyclization of the Compound

The present invention also includes cyclic compounds which are cyclic compounds.

A "cyclic compound" refers, in one instance, to a compound of the invention in which a ring is formed by the formation of a peptide bond between the nitrogen atom at the N-terminus and the carbonyl carbon at the C-terminus.

"Cyclized" also refers to the forming of a ring by a covalent bond between the nitrogen at the N-terminus of the compound and the side chain of a suitable amino acid in the sequence present therein, preferably the side chain of the C-terminal amino acid. For example, an amide can be formed between the nitrogen atom at the N-terminus and the carbonyl carbon in the side chain of an aspartic acid or a glutamic acid. Alternatively, the compound can be cyclized by forming a covalent bond between the carbonyl at the C-terminus of the compound and the side chain of a suitable amino acid in the sequence contained therein, preferably the side chain of the N-terminal amino acid. For example, an amide can be formed between the carbonyl carbon at the C-terminus and the amino nitrogen atom in the side chain of a lysine or an ornithine. Additionally, the compound can be cyclized by forming an ester between the carbonyl carbon at the C-terminus and the hydroxyl oxygen atom in the side chain of a serine or a threonine.

"Cyclized" also refers to forming a ring by a covalent bond between the side chains of two suitable amino acids in the sequence present in the compound, preferably the side chains of the two terminal amino acids. For example, a disulfide can be formed between the sulfur atoms in the side chains of two cysteines. Alternatively, an ester can be formed between the carbonyl carbon in the side chain of, for example, a glutamic acid or an aspartic acid, and the oxygen atom in the side chain of, for example, a serine or a threonine. An amide can be formed between the carbonyl carbon in the side chain of, for example, a glutamic acid or an aspartic acid, and the amino nitrogen in the side chain of, for example, a lysine or an ornithine.

In addition, a compound can be cyclized with a linking group between the two termini, between one terminus and the side chain of an amino acid in the compound, or between the side chains to two amino acids in the peptide or peptide derivative. Suitable linking groups are disclosed in Lobl et al., WO 92/00995 and Chiang et al., WO 94/15958, the teachings of which are incorporated into this application by reference.

Methods of cyclizing compounds having peptide sequences are described, for example, in Lobl et al., WO 92/00995, the teachings of which are incorporated herein by reference. Cyclized compounds can be prepared by protecting the side chains of the two amino acids to be used in the ring closure with groups that can be selectively removed while all other side-chain protecting groups remain intact. Selective deprotection is best achieved by using orthogonal side-chain protecting groups such as allyl (OAl) (for the carboxyl group in the side chain of glutamic acid or aspartic acid, for example), allyloxy carbonyl (Aloc) (for the amino nitrogen in the side chain of lysine or ornithine, for example) or acetamidomethyl (Acm) (for the sulfhydryl of cysteine) protecting groups. OAl and Aloc are easily removed by Pd and Acm is easily removed by iodine treatment.

5. Pharmaceutical Compositions and Therapeutical Methods of Treatment

The compound of the present invention can be used as an active ingredient (together with a pharmaceutically acceptable carrier) to produce a pharmaceutical composition. The pharmaceutical composition may comprise one or a mixture of two or more of the compounds of the invention in an acceptable carrier.

The pharmaceutical composition should be used for the treatment of a disease disorder or pathological condition wherein a therapeutically beneficial effect may be evident due to modulation (increase or decrease) of tissue remodeling. Typically those are diseases in which one of their manifestations (a manifestation that may be the cause or the result of the disease) is non-normal TGF-β superfamily Ser/Thr kinase receptor activity, or diseases or conditions where, although the activity is normal, a therapeutically beneficial effect may nonetheless be evident by modulating (increasing or decreasing) the activity of the TGF-β superfamily Ser/Thr kinase receptor (for example elimination of scarring which is a natural consequence of wound healing). The administration may be used for prevention of fibrosis formation; (in conditions such as post-surgical adhesions), prevention of scarring, prevention of other conditions associated with excess collagen deposition such as pulmonary fibrosis, chronic renal disease, scleroderma, liver cirrhosis, keloid formation, for decreasing fibrosis formation in the eye; for modulating neurodegeneration, and enhancement of neuronal generation, as well as regulation of bone remodeling, in particular bone healing following injury; for increasing wound and skin healing, for decreasing trauma after skin injury or for decreasing hair loss.

The term "therapeutically beneficial effect" refers either to the prevention of the disease, to alleviation of at least one undesirable effect of the disease, to lessening of the severity of the disease, or to the cure of the disease altogether. This term also refers to increased rate of healing, as well as to healing with less scarring.

The present invention also concerns a method for the treatment of an individual suffering from a disease wherein a therapeutically beneficial effect may be evident due to modulation of tissue-remodeling, the method comprising administering to the individual a therapeutically effective amount of the compound of the invention.

A "therapeutically effective amount" is the quantity of the compound that results in an improved clinical outcome as a result of the treatment compared with a typical clinical outcome in the absence of the treatment. An "improved clinical outcome" results in the individual with the disease experiencing fewer symptoms or complications of the disease, including a longer life expectancy, as a result of the treatment as well as the prevention of the disease before it occurs, decreased time to healing (bone), healing with less scarring or adhesions, decreased pain resulting from fibrosis and the like, etc.

The amount of compound administered to the individual will depend on the type and severity of the disease and on the characteristics of the individual, such as general health, age, sex, body weight and tolerance to drugs. The skilled artisan will be able to determine appropriate dosages depending on these and other factors. Typically, a therapeutically effective amount of the compound can range from about 1 mg per day to about 1000 mg per day for an adult. Preferably, the dosage ranges from about 1 mg per day to about 100 mg per day.

The compounds of the present invention can be administered parenterally. Parenteral administration can include, for example, systemic administration, such as by intramuscular, intravenous, subcutaneous, or intraperitoneal injection. Compounds which resist proteolysis can be administered orally, for example, in capsules, suspensions or tablets. The compound can also be administered by inhalation or insufflation or via a nasal spray. By a preferred embodiment, the compound is administered directly to the site where tissue-remodeling modulation should take place, such as topically to the skin (for prevention of scarring, prevention of alopecia), to the site of the broken bone (to increase healing of the bone), to the operated region (to inhibit formation of fibrosis and post surgical adhesions), for example, to the open abdominal cavity, and in a matrix surrounding silicon breast implants, to decrease scar formation, etc.

The compound can be administered to the individual in conjunction with an acceptable pharmaceutical carrier as part of a pharmaceutical composition for treating the diseases discussed above. Suitable pharmaceutical carriers may contain inert ingredients which do not interact with the compounds. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., Controlled Release of Biological Active Agents, John Wiley and Sons, 1986). The formation may be also resources for administration to bone, or in the form of salve, solution, ointment, etc. for topical administration.

6. Preparation of the Compounds

Peptide sequences for producing any of the sequence of the compounds of the invention may be synthesized by solid phase peptide synthesis (e.g., t-BOC or F-MOC) method, by solution phase synthesis, or by other suitable techniques including combinations of the foregoing methods. The t-BOC and F-MOC methods, which are established and widely used, are described in Merrifield, *J. Am. Chem. Soc.*, 88:2149 (1963); Meienhofer, Hormonal Proteins and Peptides, C. H. Li, Ed., Academic Press, 1983, pp. 48–267; and Barany and Merrifield, in The Peptides, E. Gross and J. Meienhofer, Eds., Academic Press, New York, 1980, pp. 3–285. Methods of solid phase peptide synthesis are described in Merrifield, R. B., Science, 232:341 (1986); Carpino, L. A. and Han, G. Y., *J. Org. Chem.*, 37:3404 (1972); and Gauspohl, H. et al., *Synthesis*, 5:315 (1992)). The teachings of these references are incorporated herein by reference.

As indicated above the compounds of the invention may be prepared utilizing various peptidic cyclizing techniques. Methods of cyclizing compounds having peptide sequences are described, for example, in Lobl et al., WO 92/00995, the teachings of which are incorporated herein by reference. Cyclized compounds can be prepared by protecting the side chains of the two amino acids to be used in the ring closure with groups that can be selectively removed while all other side-chain protecting groups remain intact. Selective deprotection is best achieved by using orthogonal side-chain protecting groups such as allyl (OAl) (for the carboxyl group in the side chain of glutamic acid or aspartic acid, for example), allyloxy carbonyl (Aloc) (for the amino nitrogen in the side chain of lysine or ornithine, for example) or acetamidomethyl (Acm) (for the sulfhydryl of cysteine) protecting groups. OAl and Aloc are easily removed by Pd and Acm is easily removed by iodine treatment.

Other modes of cyclization (beyond N- to C-terminal cyclization) may include: N- to backbone cyclization, C- to backbone cyclization, N- to side chain cyclization, C- to side chain cyclization, backbone to side chain cyclization, backbone to backbone cyclization and side chain to side chain cyclization.

7. Suitable TGF-β kinases

Examples of TGFβ-kinases whose activity can be modulated by the compound of the invention, as described herein, include, but are not limited to, TGFbR superfamily (ALK, BMPR, TGFbR and ACTIIA,B) and ILK. Suitable members form the ALK family include, but are not limited to, ALK1, ALK2, ALK3, ALK4, ALK5, and ALK6. BMPR-IA, BMPR-IB, BMPR-II, TGF-β RII. Specific examples of compounds comprising sequences obtained from the above are listed in the enclosed Table 1. For choosing the appropriate member of the TGFβ superfamily Ser/Thr kinase, for modulating tissue remodeling for a specific purpose, one should conduct a literature search to determine which TGF-β-kinase is involved in that specific disease.

TABLE 1

Compounds comprising sequences derived from specific TGFβ- superfamily Ser/Thr kinase receptor

| TGFβ kinase receptor | Region | Internal Ref. | SEQ ID NO. | N-terminal of compound | Sequence |
|---|---|---|---|---|---|
| ALK1 | αD | K048D801 | 1 | Palmitoyl-G | S-L-Y-D-F-L-Q-R-Q-T-L |
| | αD | K048D101 | 2 | Myristyl-G | T-H-Y-H-E-H-G-S-L-Y-D-F-L-Q-R-Q-T-L |
| | HJ-loop | K048H101 | 3 | Myristyl-G | G-I-V-E-D-Y-R-P-P-F |
| | HJ-loop | K048H102 | 4 | Myristyl-G | G-I-V-E-D-Y-R-P-P |
| | HJ-loop | K048H103 | 5 | Myristyl-G | G-I-V-E-D-Y-R-P |
| | HJ-loop | K048H104 | 6 | Myristyt-G | V-N-G-I-V-E-D-Y-R-P |
| | HJ-loop | K048H105 | 7 | Myristyl-G | I-A-R-R-T-I-V-N |
| | HJ-loop | K048H106 | 8 | Myristyl-G | I-A-R-R-T-I-V-N-G-I-V |
| | HJ-loop | K048H107 | 9 | Myristyl-G | T-I-V-N-G-I-V |
| | HJ-loop | K048H901 | 10 | Stearyl-G | G-I-V-E-D-Y-R-P-P-F |
| | B4–B5 region | K048B901 | 11 | Stearyl-G | D-M-T-S-R-N-S-S-T |

TABLE 1-continued

Compounds comprising sequences derived from specific TGFβ- superfamily Ser/Thr kinase receptor

| TGFβ kinase receptor | Region | Internal Ref. | SEQ ID NO. | N-terminal of compound | Sequence |
|---|---|---|---|---|---|
| TGFβRII | αD | K093D801 | 12 | Palmitoyl-G | N-L-Q-E-Y-L-T-R-H-V-I |
|  | αD | K093D101 | 13 | Myristyl-G | T-A-F-H-A-K-G-N-L-Q-E-Y-L-T-R-H-V-I |
|  | HJ-loop | K093H101 | 14 | Myristyl-G | G-E-V-K-D-Y-E-P-P-F |
| ILK | HJ-loop | K107H901 | 15 | Stearyl-G | G-L-V-T-R-E-V-P-F |
| ACTRIIA | αD | K095D801 | 16 | Palmitoyl-G | S-L-S-D-F-L-K-A-N-V |
|  | HJ-loop | K095H101 | 17 | Acetyl-G | P-V-D-E-Y-M-L-P-F |
|  | B4–B5 | K095B901 | 18 | Stearyl-G | E-K-R-G-S-N-L-E-V |
| ALK3 | αD | K098D801 | 19 | Palmitoyl-G | S-L-Y--D-F-L-K-C-A-T-L |
|  | αD | K098D802 | 20 | Palmitoyl-G | S-L-Y-D-F-L-K-S-A-T-L |
|  | HJ-loop | K098H101 | 21 | Myristyl-G | G-I-V-E-E-Y-Q-L-P-Y |
|  | HJ-loop | K098H901 | 22 | Stearyl-G | G-I-V-E-E-Y-Q-L-P-Y |
|  | A-region | K098A101 | 23 | Myristyl-G | G-L-M-R-H-E-N-I-L-G-F |
|  | B4–B5 region | K098B901 | 24 | Stearyl-G | D-I-K-G-T-G-S-W-T |
| ALK4 | αD | K099D801 | 25 | Palmitoyl-G | S-L-F-D-Y-L-N-R-Y-T-V |
|  | HJ-loop | K099H101 | 26 | Myristyl-G | G-Q-V-H-E-E-Y-Q-L-P-Y |
|  | B4–B5 region | K099B901 | 27 | Stearyl-G | D-N-K-D-N-G-T-W-T |
| BMPRII | αD | K116D102 | 28 | Myristyl-G | L-S-K-Y-L-S-L-H-T-S |
|  | αD | K116D001 | 29 | Acetyl-G | L-C-K-Y-L-S-L-H-T-S |
|  | HJ-loop | K116H801 | 30 | Palmitoyl-G | G-E-S-V-P-E-Y-Q-M-A-F |
|  | B4–B5 region | K116B901 | 31 | Stearyl-G | D-E-R-V-T-A-D-G-R-M |

8. Determination of Tissue-remodeling Modulating Activity

Although final verification of tissue remodeling can be achieved only when testing the compound's effect on the tissue, a good indication as regards the tissue remodeling activities can be obtained by incubating the candidate compounds with cells, which have one or more of their physiological properties controlled by the TGF-β-kinase, or with a cell-free system comprising the various cellular components of the TGF-β-kinase signaling pathway. Verification or testing for actual tissue remodeling activities can be determined with tissues which comprise cells that are generated and regenerated or with animal models, wherein at least one physiological property is controlled by TGF-β-kinase, all the above being collectively referred to as "test assay".

It should be appreciated that some of the compounds that comprise sequences (a)–(g) above have better tissue-remodeling modulating activities than others. Some of the conservative substitutions in the essential positions may diminish tissue-remodeling modulating activities, while other such conservative substitution in the essential positions may improve these modulating activities. The same is true also for deletions, substitutions (both conservative and non-conservative) in non-essential positions, as well as to chemical modifications of the side chains (in any position) or insertions. In addition the type and size of the non-amino acid portion of the compounds, such as a hydrophobic moiety in one of its terminals may diminish or increase kinase-modulating activities. The modulating activities may be determined by using one of the assays below.

8.1 Cellular Assay

It can be readily determined whether a compound modulates the activity of a TGF-β-kinase by incubating the compound with cells which have one or more cellular activities controlled by the kinase. The cells are incubated with the candidate compound to produce a test mixture under conditions suitable for assessing the activity of the specific TGF-β-kinase. The activity of the TGF-β is assessed and compared with a suitable control, e.g., the activity of the same cells incubated under the same conditions in the absence of the candidate compound (or in the presence of a control compound). A greater or lesser activity of the TGFβ-kinase in the test mixture compared with the control indicates that the candidate compound modulates the activity of the TGF-β-kinase and thus may be a likely candidate to modulate tissue remodeling. Actual tissue remodeling will later have to be verified of course in tissue culture or in vivo.

Suitable cells for the assay include normal cells which express the TGF-β-kinase, cells which have been genetically engineered to express a TGF-β-kinase, malignant cells expressing a TGF-β-kinase or immortalized cells that express the TGF-β-kinase.

Conditions suitable for assessing the activity include conditions suitable for assessing a cellular activity or function under control of the TGF-β-kinase. Generally, a cellular activity or function can be assessed when the cells are exposed to conditions suitable for cell growth, including a suitable temperature (for example, between about 30° C. to about 42° C.) and the presence of the suitable concentrations of nutrients in the medium (e.g., amino acids, vitamins, growth factors or of specific activators such as cytokines, hormones and the like).

In another aspect, the activity of certain kinases can be evaluated by growing the cells under serum deprivation conditions. Cells are typically grown in culture in the presence of a serum such as bovine serum, horse serum or fetal calf serum. For example, it is possible to access the number of cells (proliferation) of HFL-1 cell live grown for 48 hours under cell deprivation conditions and then supplied with the candidate compound.

It is also possible to test the proliferation (determined for example by cell number as determined by methylene-blue dye) of immortal cell lines, such as for example, MDA-231 and MCF-7 in the presence of the candidate compound.

Generally, the activity of the TGF-β-kinase in the test mixture is assessed by making a quantitative measure of the cellular activity which the TGF-ββ-kinase controls. The cellular activity can be, for example, cell proliferation, increase or decrease of the following cells: fibroblasts of various tissue origin; osteoblasts; neuronal cells, embryonic cells, oocytes and sperm-producing cells, etc. Modulating activity is assessed by measuring cellular proliferation, for example, by comparing the number of cells present after a given period of time with the number of cells originally present.

If cells are being used in which the TGF-β-kinase receptor controls cell differentiation (e.g., activity is assessed by measuring the degree of differentiation). Activity can be assessed the degree to which neurites are extended. Activity can also be assessed by the extent to which gene expression; cell morphology or cellular phenotype is altered (e.g., the degree to which cell shape is altered or the degree to which the cells assume a spindle-like structure). One example of a change in cellular morphology is reported in the application entitled "SHORT PEPTIDES WHICH SELECTIVELY MODULATE INTRACELLULAR SIGNALING" (filed on May 21, 1997, U.S. application Ser. No. 08/861,153), which discloses that certain peptide derivatives of the HJ loop of protein tyrosine kinases can cause vascular smooth muscle cells to become elongated and assume a spindle-like shape. Tissue cultures may also be used to access activity, for example, by determining the ECM production of tissue, etc.

8.2 Phosphorylation of substances

Where the substrates of the kinases are known (such as when the specific SMADs of the TGF-β-kinase are shown), it is possible to assess the kinase activity and the changes in this activity as compared to control, by determining the phosphorylation level of the substrate protein (for example of the SMAD proteins). Cells known to express the TGFβ kinase are incubated with a candidate compound for modulating the TGFβ-kinase activity. Then the cells are lysed, the protein content of the cells is obtained and separated on a SDS-PAGE. The substrates can be identified by use of suitable molecular weight markers, or by using suitable antibodies. The level of substrate phosphorylation can be determined by using anti-phosphotyrosine antibodies, either conjugated to a suitable label or further reacted with a label-bearing antibody (see Fujimoto et al., *Immunity*, 13:47–57 (2000)).

Alternatively phosphorylation may be determined in a cell-free system by incubating membranal components comprising TGFβ-kinase, its substrate and candidate compounds for modulating TGFβ-kinase activity in the presence of ATP under conditions enabling phosphorylation. The proteins are then subjected to SDS-PAGE, transferred to nitrocellulose followed by immunoblotting by anti-phosphotyrosine antibody. Alternatively it is possible to use [γ-$^{32}$p] ATP and quantify the amount of radioactivity in cooperated in the substrate (See Fujimoto et al., *The J. of Immunol.* 7088–7094 (1999).

It should be appreciated that the specific assay should be designed in accordance with the activities of the specific TGFβ-kinase to be modulated by the compound.

8.3. Tissue or in vivo Assay

Suitable assays for determining modulation of tissue remodeling are specified in Examples 1 to 7 below.

It is possible that future research will reveal that certain disease conditions, whose underlying causes are presently unknown, are brought about by the over activity of under activity of cellular functions controlled by TGFβ-kinase. These diseases can be treated by the compounds of the invention.

9. Tiussue Remodeling 9.1 Alopecia

Alopecia is a diseased state which results in hair loss. Alopecia can be an undesired side effect of chemotherapy and/or radiation therapy. Hair loss from chemotherapy is usually temporary while hair loss due to radiation therapy is usually permanent.

TGFβ is found in anagen hair follicles, and is secreted immediately prior to hair entry into the catagen phase. Similary, BMP-2 expression by mature follicles coincides with the cessation of cell proliferation. These two findings implicate an important role for these compounds in the regulation of hair growth (Peeus, D., Pittelkow, M. R., "Growth factors in hair organ development and the hair growth cycle", *Dermatol. Clin*, 14(4):559–572, 1996). Moreover, overexpression of TGF-β1 in the epidermis of transgenic mice results in significantly fewer hair follicles and a thinned interfollicular epidermis (Sellheyer K, Bickenbach J R, Rothnagel J A, Bundman D, Longley M A, Kreig T, Roche N S, Roberts A B, Roop DR. "Inhibition of skin development by overexpression of transforming growth factor B1 in the epidermis of transgenic mice", *Proc Natl Acad Sci USA* 1993; 90:5237–5241). Likewise, BMP-4 overexpressed in transgenic mice is shown to be ectopically expressed in the outer root sheath and results in complete deficiency of hair growth after the first growth cycle and subsequent progressive balding, (Blessing M, Nanney L N B, King L. E., "Transgenic mice as a model to study the role of TGF-β-related compounds in hair follicles", *Genes Dev.* 1993, 7(2): 204–215; Hussein A M, Jimenez J J, McCall C A, Yunis A. A., "Protection from chemotherapy-induced alopecia in a rat model", *Science* 1990, 249:1564–1566).

Compounds of the invention can be effective in the treatment of alopecia. For example, as described in Example 2, compounds can be used to treat chemotherapy-induced alopecia. The compound may be used to treat other types of alopecia such as alopecia caused by, chemotherapy, radiotherapy, autoimmune diseases, old age, or genetic causes. Compounds of the present invention can also be used as co-treatment with radio- or chemo-therapy in cancer patients to prevent hair loss associated with such treatment.

9.2 Fibrosis and Scarring

Fibrosis and scarring is the result of deposition of fibrous tissue. It is characterized by excessive deposition of collagen, as well as other components of extracellular matrix. These processes may follow injury or surgery to the skin, epidermis or corrective tissue and is many times an undesired result of plastic surgery, such as side effect of breast implantation. In addition, blacks are many times prone to formation of keloids following even minor skin injury. Fibrosis also characterizes various diseases of internal organs, such as liver cirrhosis, pulmonary cirrhosis, and nephropathy, and the same mechanism of excess deposit of fibrous tissue may be responsible for those conditions.

For example, as described in Example 3, compounds of the invention may be used to treat skin scarring formed after skin burns, after cosmetic operations (including implantation of silicon graphs in breasts), or due to accidents. In addition, the compounds can be used to treat post-operative abdominal adhesions.

The present invention can also be used to treat other diseases where the pathology involves deposition of connective tissue leading to scarring and fibrosis, i.e., liver cirrhosis, pulmonary fibrosis, renal scarring, hyperkeratosis.

9.3 Wound Healing

The process of wound healing involves inflammation, epithelial and mesenchymal proliferation, and extracellular matrix synthesis and remodeling. In all post-natal animals, scar formation invariably involves excessive extracellular matrix synthesis and remodeling. TGF-β1 has been shown to be instrumental in both the initiation and the resolution of inflammatory and immune events. TGF-β1 is an important regulator of the extracellular matrix (ECM), stimulating fibroplasia and collagen deposition, inhibiting ECM degrading proteases and upregulating the synthesis of protease inhibitors. Since all these processes are involved in the wound repair processes, the role of TGF-β1 in regulating these activities and wound healing is of major clinical significance. An important discovery was the observation that embryonic or early fetal wounds heal without scars. Reduced inflammatory response and hence altered cytokine profile, reduced wound angiogenesis and absence fibrin clots, characterize the fetal scar-free phenotypes. In normal skin TGF-β1 is produced by keratinocytes and by dermal capillaries. TGF-β3 is constitutively expressed in epidermal keratinocytes, while TGF-β2 is not expressed in these cells. Following wounding, the levels of TGF-βs is altered significantly. There is a cross-regulation of TGF-β1 and TGF-β3 isoforms during wound healing: when TGF-β3 is high, TGF-β1 is low and vice versa. However, there are profound differences between embryo and adult TGF-βs ratios. In the embryo, where the ratio of TGF-β3 to TGF-β1 is high, wounds heal with minimal scarring. The neutralization of TGF-β1 by antibodies reduces the inflammatory and angiogenic responses and alters the deposit of ECM, without reducing the tensile strength of the wound. Thus, reducing scar formation and generating a nearly normal dermal architecture as compared with untreated wounds.

9.4 Cell Proliferation

Control of cell proliferation is important in many biological functions. For example, it is well known that cancer is the result of uncontrolled cell proliferation and there is a known connection between the TGFβ pathway and cellular proliferation, Blode, G. C., Schiemann, W. P. and Lodish, H. F.: Role of Transforming Growth Factor β in Human Disease, *The New England J. of Med.*, 342:1350–1358, 2000. Reiss, M, TGFβ and Cancer, *Microbes and Infection*, 1:1327–1347, 1999. Massague, J., Blain, S. W. and Lo, R. S.: TGFβ Signaling in Growth Control, Cancer, and Heritable Disorders, *Cell*, 103:295–309, 2000.

9.5. A model for Testing-tissue-remodeling Modulation—Neuronal Crest Migration

Neural crest cells are a group of embryonic cells that separate from the neural plate during neurulation and migrate to generate several different lineages of adult cells including the spinal and autonomic ganglia, the glial cells of the peripheral nervous system and the non-neuronal cells, such as chromaffin cells, melanocytes and some hematopoietic cells. Neuronal crest migration can be used as a search tool for screening for active compounds of the invention, wherein compounds which modulate neuronal cell migration are candidates for modulating of tissue remodeling in general. More specifically, this assay can identity compounds that modulate (mimic or inhibit) BMP's activities.

9.6 Bone Remodeling

In Example 7, compounds can be generated to modulate bone remodeling and in particular enhance bone healing after trauma, surgery and reduced DVT. The compounds may be placed in the region of the fractured bone, for example in a viscous carrier such as methylcellulose from which it can diffuse to the surrounding tissue. The treatment can be used also for enhancing bone growth were a relatively large bone segment is missing, a condition termed "non-union". The treatment may also be used to augment the maxillary sinus floor. Many time, when it is desired to insert an implant which serves as a base to artificial teeth into the maxillary sinus floor, the floor. collapses. This problem is especially prominent in elderly individuals. Augmentation of the maxillary sinus floor thus will enable to anchor the implant much more firmly, allowing subsequent attachment of a base for artificial teeth.

The invention is illustrated by the following examples which are not intended to be limiting in any way.

EXAMPLE 1

Prevention of Chemotherapy-Induced Alopecia

An experimental model for alopecia has been developed by Hussein, et al. (*Science* 1990; 249:1564–1566), the teachings of which are incorporated herein by reference. Briefly, eight-day old Sabra rats, randomly divided, were injected intraperitoneally (i.p.) with 0.5 mg/rat cytosine arabinoside (Ara-C) in PBS+0.1% BSA, for 7 days. Compounds, comprising TGF-β-derived sequences were subsequently injected subcutaneously (s.c.) on days 1, 4 and 7 with a single dose of 2.5 mg (in 0.5 ml of PBS+0.1% BSA). Additionally, a dose response assay was carried out with doses of 0.1, 0.5 and 2.5 mg (in 0.5 ml of PBS+0.1% BSA). Treatment of rats by local application of the compounds was carried out by applying compounds dissolved in glycerol to the dorsal skin of the rats at a dose of 2.5 mg per day, for 8 days. Alopecia was evaluated on day 9. Corresponding full thickness skin sections were taken for histology.

The results are shown in FIG. 1, wherein two administrators (c) of a compound being SEQ ID NO: 3 (K048H101 in Table 1), comprising a peptide derivative of ALK-1 receptor and are SEQ ID NO: 22 (K098H901 in Table 1), comprising a peptide derivative of ALK-3 receptor, are demonstrated.

Figure 2:
FIG. 2 illustrates the dose response inhibition of chemotherapy-induced alopecia by a compound comprising ALK peptide/peptide variant, (K048H901).

As can be seen in FIG. 1, subcutaneous injections of the compounds comprising TGF-β-derived peptides prevent chemotherapy-induced alopecia. Local application of the compounds was also proved to be useful in preventing alopecia and resulted in less than 50% hair loss. The results for SEQ ID NO: 10 (K048H901 in Table 1) dose response experiment are shown in FIG. 2. As can be seen in FIG. 2, SEQ ID NO: 10 (K048H901 in Table 1) prevents chemotherapy-induced alopecia in a dose dependent manner. Complete protection was achieved with the highest dose of compounds. At lower doses, hair loss was partial and proportional to the given dose.

Figure 3A:
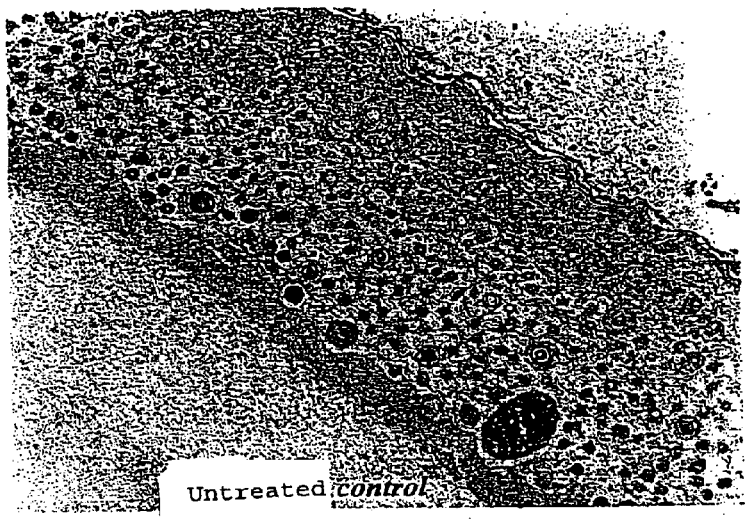
FIG. 3 shows histological skin sections which demonstrate the inhibition of hair follicle loss by a compound comprising ALK peptide/peptide variant, (K098H101); A—untreated control, B—Ara-C treated control, C—Ara-C together with the compound of the invention.
Figure 3B:
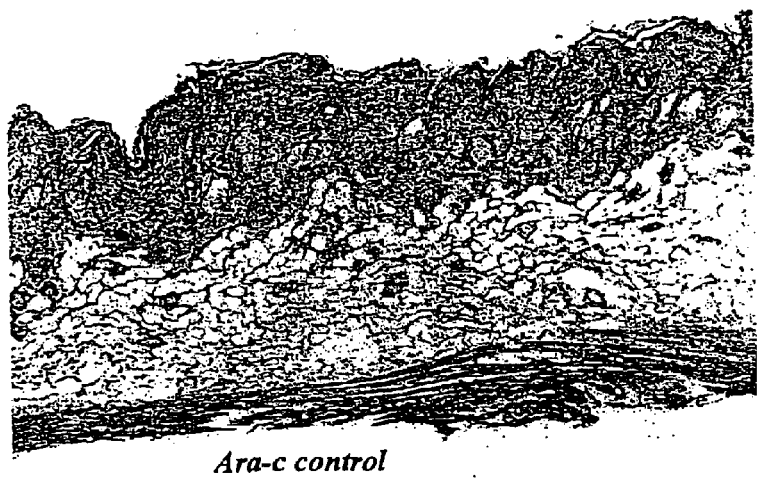
Figure 3C:
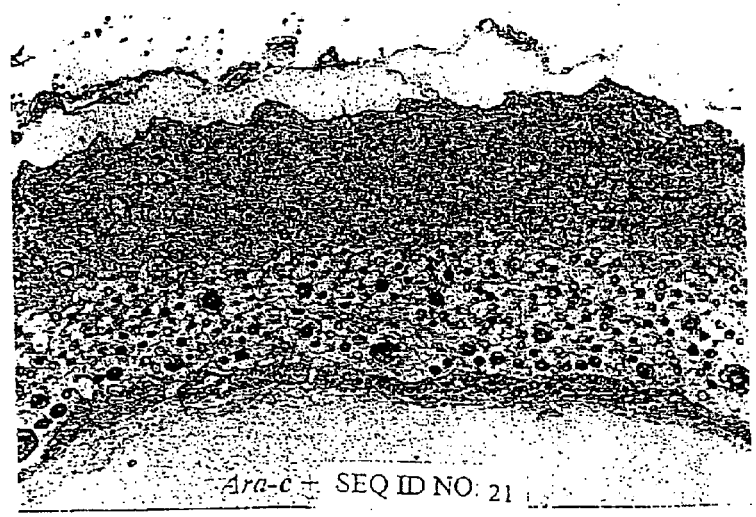

FIG. 3 depicts representative histology of skin sections taken from the experimented rats. As can be seen in FIG. 3, treatment with Ara-C causes loss of hair follicles in the skin. However, simultaneous treatment with the compounds of the invention (SEQ ID NO:21) prevents this loss of follicles. The skin section taken from animals treated with Ara-C and the compounds comprising TGF-β-derived peptide is similar to that of the untreated control.

EXAMPLE 2

Reduction of Scarring

Skin burns were induced by a single dorsal s.c injection of 0.15 ml of 0.2% formic acid in 100% ethanol to BalbC mice. The treated animal group received 0.15mg of the compounds comprising TGF-β-derived peptide dissolved in the above mixture. The animals were sacrificed 13 days post-burn and histology was performed on the healing skin. Collagen production following burns was quantitized in both control and treated mice, according to the method of Lopez-De Leon and Rojkind (*J. Histochem Cytochem.* 33(8): 737–743, (1985)).

As can be seen in Table 2, collagen formation was inhibited by local treatment with SEQ ID NO: 3 (K048H101 in Table 1); 13 days post-burn, collagen levels in treated animals were 35% lower than in controls.

TABLE 2

In-Vivo Inhibition of Collagen Formation by SEQ ID NO: 3 (K048H101 in Table 1) Following Skin Burns (Relative Amount of Tissue Collagen/Total Protein)

|  | CONTROL: ETHAN + FORMIC ACID* | K048H101 0.15 MG/SITE IN ETHANOL + FORMIC ACID |
|---|---|---|
| 13 days post burn | 2.59 (100%) | 1.68 (65%) |

*formic acid 0.2% in ethanol 100%

EXAMPLE 3

Reduction of Abdominal Adhesion Formation

Abdominal adhesion formation was previously described by Frazeir-Jessen and Kovacs (*J. Immunol. Meth.* 162:115–121 (1993)). The teaching of which are incorporated herein by reference. A suspension of 40 mg talc in 1 ml PBS was injected i.p. to C57 black mice. The treated animal group received 5 mg of SEQ ID NO: 22 (K098H901 in Table 1) comprising an ALK-3-derived peptide, dissolved in the above suspension. The animals were sacrificed 14 days post injection. The numbers of adhesions formed in each mouse were counted. As can be seen in Table 4, the number of abdominal adhesions formed within 14 days post treatment was reduced by more than 60% in animals that received SEQ ID NO: 22 (K098H901 in Table 1) simultaneously with the talc injection.

TABLE 3

In Vivo Inhibition of Abdominal Adhesion Formation by a compound comprising SEQ ID NO: 22 (K098H901 in Table 1) following Talc Injection

| | Number of adhesions per mouse | | | | |
|---|---|---|---|---|---|
| Treatment | Between Intestine and wall | Between intestine loops | Between intestine and liver | Between intestine and other organs | Average number of adhesions per mouse |
| PBS (1 ml, i.p.) | — | — | — | — | 0 |
| Talc (40 mg/ml) | 1 | — | 1 | 1 | 5.33 |
|  | 4 | — | 1 | — |  |
|  | 3 | 5 | — | — |  |
| talc + | — | — | 1 | 2 | 2 |

TABLE 3-continued

In Vivo Inhibition of Abdominal Adhesion Formation by a compound comprising SEQ ID NO: 22 (K098H901 in Table 1) following Talc Injection

| | Number of adhesions per mouse | | | | |
|---|---|---|---|---|---|
| Treatment | Between Intestine and wall | Between intestine loops | Between intestine and liver | Between intestine and other organs | Average number of adhesions per mouse |
| K098H901 (5 mg/ml) | 1 — | — — | — — | 1 1 | |

EXAMPLE 4

Fibroblast Cell Proliferation

Human Fetal lung fibroblasts (HFL-1) were obtained from the American Type Culture Collection (Manassa, Va.). Culture medium was prepared from F-12K (Gibco), penicillin/streptomycin/glutamine (penicillin—100 U/ml; streptomycin—100 Uml; glutamine—2 mM), 0.1% fetal calf serum and 50 mg/ml ascorbic acid. A suspension of HFL-1 cells at $2.22 \times 10^5$ cell/ml was prepared in the above-described culture medium.

A series of stock solution was prepared by diluting a 10 mM solution of the tested compound, comprising the TGF-β peptide, in 100% DMSO, with phosphate buffered saline (PBS) containing 0.1% BSA. The concentration of the compounds in each stock solution was adjusted to nine times the desired concentration of the TGF-β containing compounds in the assay mixture. Twenty μl of compound stock solution were placed at the bottom of each well in a 96-well flat bottom tissue culture plate, six replications for each concentration. BSA solution containing 1% DMSO with no added peptide served as a control. 180 μl of the HFL-1 cell suspension were added to each well (40,000 cells per well). The cells were incubated with the compound (final concentrations of 0–10 μM), for 48 hours at 37° C. in a 5% $CO_2$ humidified incubator. At the end of the incubation the cells were fixed with buffered formaline (200 μl/well) for 1 h at room temperature. The wells were then washed with 0.1M, pH 8.5 borate buffer (200 μl/well). The fixed cells were stained with freshly filtered 1% methylene blue solution (50 μl/well) for 15 min at room temperature. Excess dye was washed with tap water. Cell-bound dye was eluted with 200 μl of 0.1M HCL per well. The O.D. was read at 595 nm to determine the number of cells per well. The procedure for counting cells is described in greater detail in Oliver et al., *J. of Cell Sci.* (1989) 92:513, the teaching of which are incorporated herein by reference.

Figure 4:
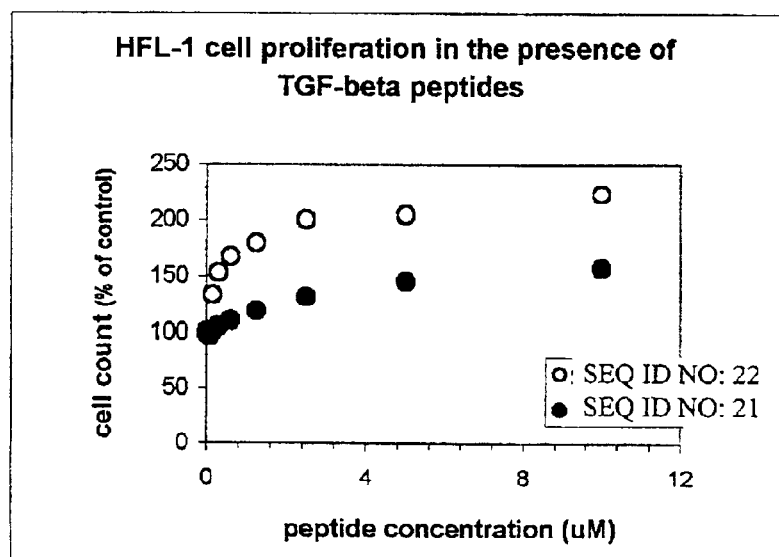
FIG. 4 illustrates the enhancement of human fetal lung fibroblasts (HLF-1) cell proliferation by a compound comprising ALK peptide/peptide variant, (K098H101 and K099B901).

The results for a compound comprising TGF-β peptides SEQ ID NO: 22 (K099B901 in Table 1) (an ALK4-derived peptide) and SEQ ID NO: 21(K098H101 in Table 1) (an ALK3-derived peptide) are shown in FIG. 4. As can be seen, these compounds had a marked effect on fibroblast cell proliferation.

EXAMPLE 5

Enhancement of Migratin of Neural Crest Cells from Neural Primordia by Compounds comprising TGF-β Peptides—A Model for Screening Active Compounds The procedure for explants of neural primordia is described in greater detail in Sela-Donenfeld and Kalcheim (*Development*, 126(21): 4749–4762 (1999)), the teaching of which are incorporated herein by reference.

The trunk region of 16 somite-old quail embryos was separately sectioned at the level of the segmental plate plus the last 2 epithelial somite pairs. Neural primordia consisting of the neural tube and premigratory neural crest cells were isolated from adjacent tissues with 25% pancreatin in PBS, transferred to PBS supplemented with 5% newborn calf serum to stop enzymatic activity and washed in serum-free culture medium prior to explanation. The neural primordia were then explanted onto multi-well chamber slides that were pre-coated with fibronectin (50 µg/ml) for 1 hour. The neural primordia were cultured in 50 µl serum-free SFRI medium (Berganton, France) in the absence or presence the tested peptide, in a final concentration of 5 µM and incubated in a humid chamber for 24 hours. At the end of the incubation, the primordia were gently washed with PBS and fixed with Bouin's fluid, washed 3 times with PBS and immunostained with 50 µl monoclonal antibodies against HNK-1 for 1 hour at room temperature. Excess HNK-1 antibodies were washed 3 times with PBS. The samples were further incubated with 50 µl of a secondary fluorescent antibody, GAM-FITC for 1 hour at room temperature. Excess antibodies were washed 3 times with PBS. The slides were dried and covered.

The results for a compound comprising TGF-β peptide SEQ ID NO: 27 (K099B901 in Table 1) are shown in FIG. 5.

Figure 5A:
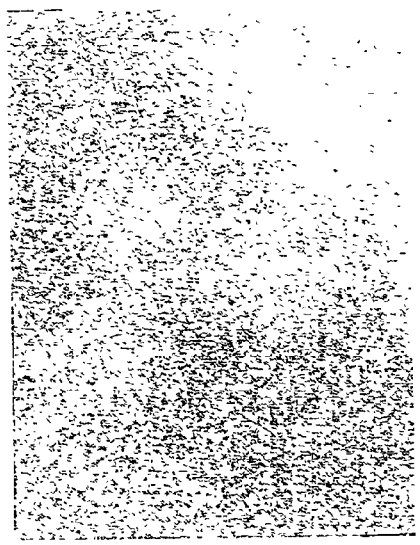
FIG. 5 illustrates the enhancement of neural crest cell migration from cultured quail neural tubes by a compound comprising ALK peptide/peptide variant, (K099B901).
Figure 5B:
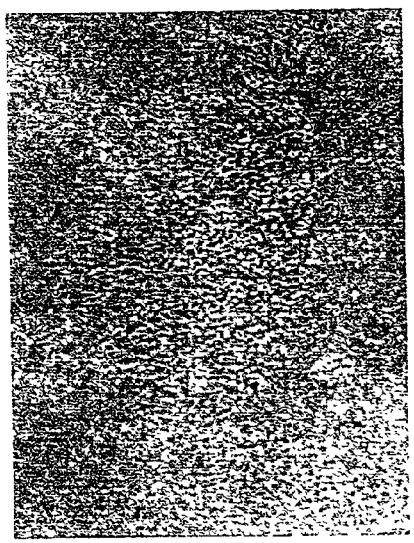
Figure 5C:
Figure 5D:

As can clearly be seen in FIGS. 5A and 5B, the addition of SEQ ID NO: 27 (K099B901 in Table 1) to neural primordia explants caused a remarkable outgrowth of HNK-1-positive neural crest cells from the explant as compared to control.

EXAMPLE 6

Enhancement of Emigration of Neural Crest Cells From Neural Primordia; Mimicking the Effect of BMP The onset of neural crest cell migration is a complex morphogenetic process. A balance between BMP-4 and its inhibitor noggin regulate emigration of neural crest progenitors from the neuroepithelium. We employed this knowledge to identify peptides derived from the TGF-β superfamily, that mimic BMP's action.

The procedure for explants of neural primordia is described in greater detail in Sela-Donenfeld and Kalcheim (*Development*, 126(21): 4749–4762 (1999)), the teaching of which are incorporated herein by reference.

The trunk region of 16 somite-old quail embryos was separately sectioned at the level of the segmental plate plus the last 2 epithelial somite pairs. Neural primordia consisting of the neural tube and premigratory neural crest cells were isolated from adjacent tissues with 25% pancreatin in PBS, transferred to PBS supplemented with 5% newborn calf serum to stop enzymatic activity and washed in serum-free culture medium prior to explanation. The neural primordia were then explanted onto multi-well chamber slides that were pre-coated with fibronectin (50 µg/ml) for 1 hour. The neural primordia were cultured in 50 µl of either serum-free CHO-S-SFMII medium (GibcoBRL, USA) or condition medium of noggin producing-CHO cells, in the absence or presence the tested compound, in a final concentration of 5 µM and incubated in a humid chamber for 24 hours. At the end of the incubation, the primordia were gently washed with PBS and fixed with Bouin's fluid, washed 3 times with PBS, dried and covered.

The results for a compound comprising ALK-3-derived peptide SEQ ID NO: 23 (K098A01 in Table 2) are shown in FIG. 6.

Figure 6A:
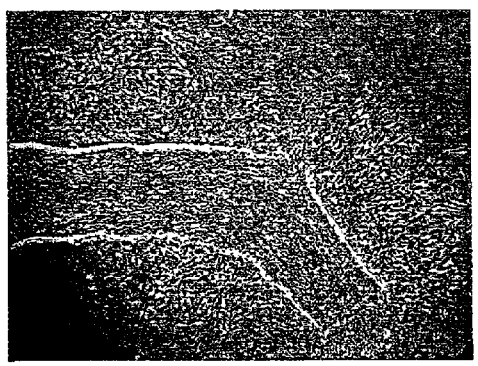
FIG. 6 illustrates that the compound comprising ALK peptide/peptide variant, K098A101, overcomes the inhibition of neural crest cell migration caused by noggin.
Figure 6B:
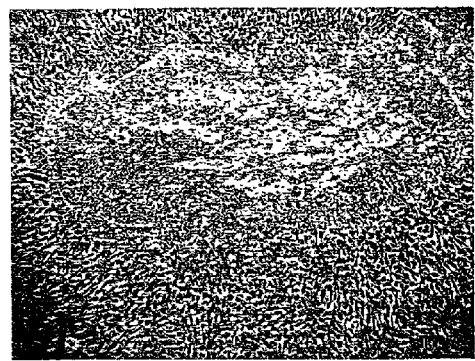
Figure 6C:
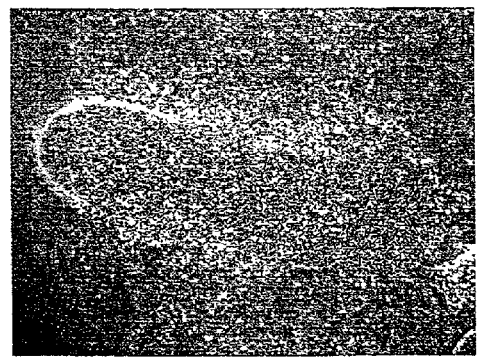
Figure 6D:
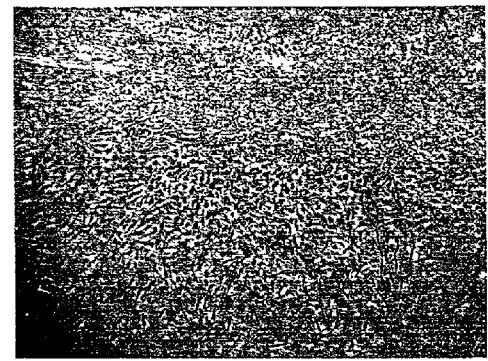

As can be seen in FIG. 6A, neural crest cells naturally migrate out of the tube. In the presence of the peptide (FIG. 6B), the number of migrating cells is higher. Noggin, which is a specific inhibitor of BMP-4, blocks the neural crest migration (FIG. 6C). However, in the presence of noggin and peptide (FIG. 6D), the peptide overcomes this inhibition and induces neural crest migration.

EXAMPLE 7

Enhancement of Bone Healing

Rabbit ulnar osteomy models described by Bouxsein et al. at the 45$^{th}$ Annuarl Meeting, Orthopedic Research Society, Anaheim, Calif. (1999), was employed to assess the ability of compounds, comprising TGF-β peptides, to accelerate bone remodeling.

Bilateral mid-ulnar osteotomies were made in the front limbs of male New Zealand White rabbits using an oscillating saw. The preparation of the tested compound was as follows: 40 mg of compound were dissolved in 200 µl of DMSO (Sigma) and 800 µl of double distilled water. The solution was mixed with 100 mg of methyl cellulose (Sigma) and 100 mg of carboxymethyl cellulose (Serva). The same mixture without the compound served as a vehicle control.

The mixture containing the compound comprising the TGF-β-containing compound, or the vehicle alone, (0.3 cm$^3$) was locally applied to the fractured area. An untreated osteotomy served as an additional control. Radiographs of the ulna were taking weekly for 4 weeks in order to assess the callus area: it's onset of formation, size and density. Criteria for bone-healing grading were determined based on x-ray imaging. The rabbits were then sacrificed and the fractured areas were taken for bone histology. The bone tissue was fixated in 4% formaldehyde and then soaked in 10% formic acid for decalcification. The decalcified tissue was imbedded in paraffin wax, serially sectioned at 5 µ and stained with indigo-carmine. Bone tissue from a similar experiment, was taken for histology 2 weeks post operation, similarly processed and stained with Masson-tri-chrome dye.

Results

The peptides present in the compounds used in this series of experiments were:
  SEQ ID NO: 16 (K095D801 in Table 1), and ACRIIA derived peptide.
  SEQ ID NO: 21 (K098H101 in Table 1), an ALK-3 derived peptide.
  SEQ ID NO: 27 (K099B901 in Table 1), an ALK-4 derived peptide.
  And a combination of SEQ ID NO: 16 (K095D801 in Table 1) and SEQ ID NO: 27 (K099B901).
  Each point represents the average of 8 limbs.

Figure 7:
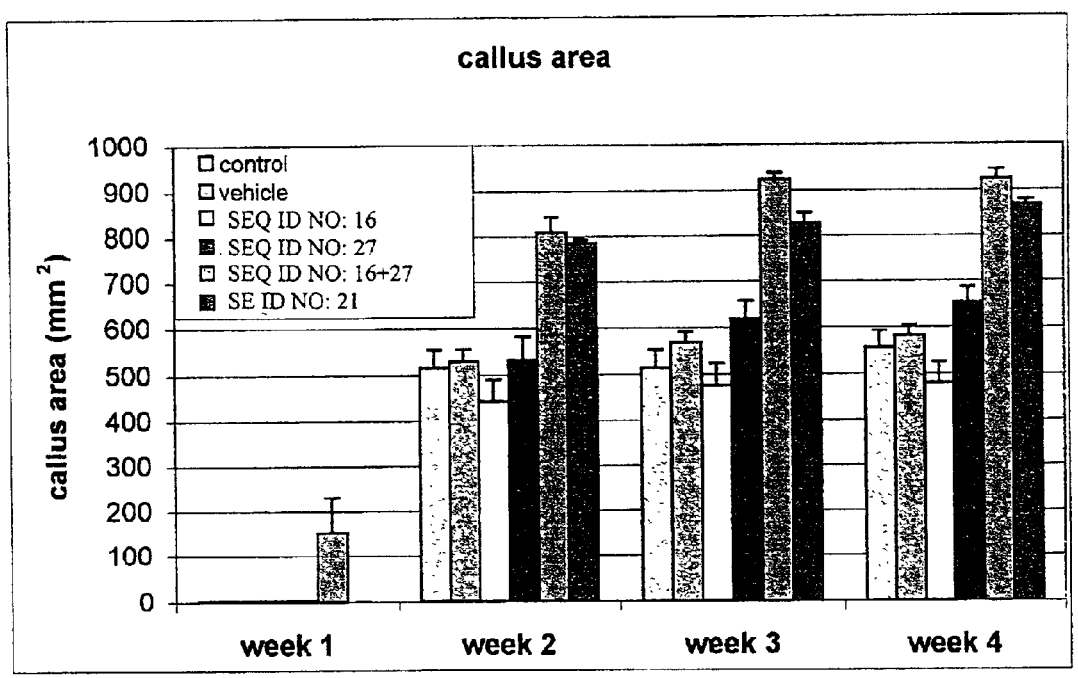
FIG. 7 illustrates the enhancement in the rate of bone callus growth in rabbit mid-ulna osteotomies by a compound comprising ALK peptide/peptide variant, K098H101, K099B901, and a compound comprising the ACR-IIR peptide/peptide variant, K095D801.

AS can be seen in FIG. 7, the application of either combined peptides SEQ ID NO: 16 (K095D801 in Table 1) and SEQ ID NO: 27 (K099B901 in Table 1), or peptide SEQ ID NO: 21 (K098H101 in Table 1) to the fracture area, resulted in a larrger callus area, throughout the entire experiment interval.

Figure 8:
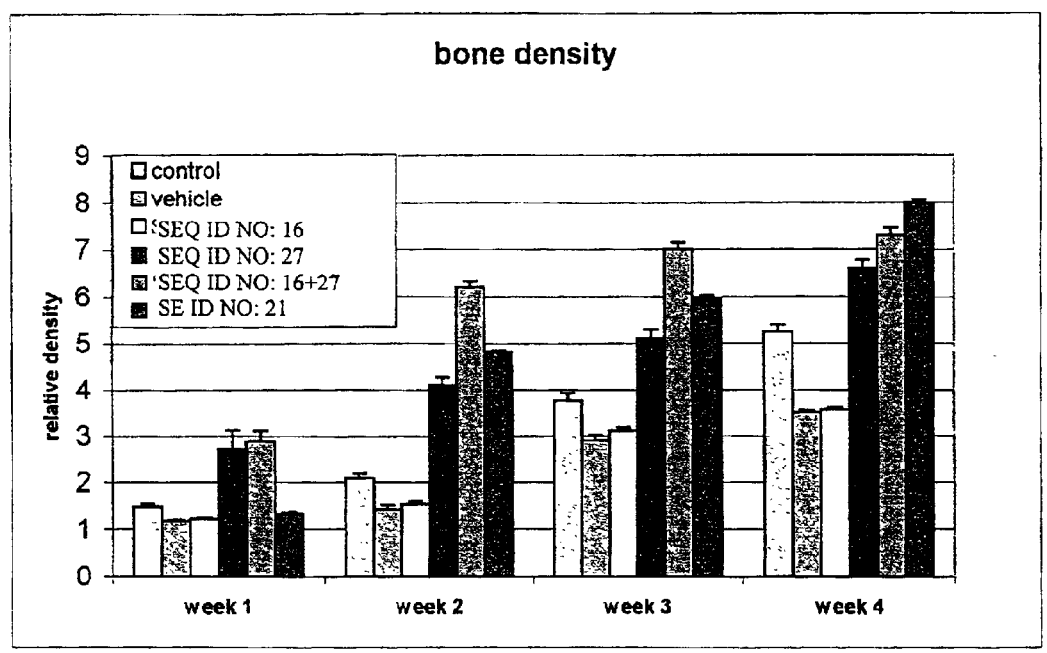
FIG. 8 illustrates the enhancement in bone density in rabbit mid-ulna osteotomies by a compound comprising ALK peptide/peptide variant, (K098H101, K099B901), and a compound comprising the ACR-IIR peptide/peptide variant (K095D801).

As can be seen in FIG. 8, the application of compounds SEQ ID NO: 27 (K099B901 in Table 1), SEQ ID NO: 21

(K098H101 in Table 1) and the combination of compounds pf SEQ ID NO: 16 (H095D801 in Table 1) and SEQ ID NO: 27(K099B901 in Table 1) to the fracture area result in a higher bone density compared to that of the controls. This difference is already noticeable within the first week and becomes more significant with time.

Bone Healing Grading was Determined According to the Following Criteria 0 no callus
1 primary callus response at one end of bone
2 primary callus response at both ends of bone
3 primary callus response at both ends of bone plus soft tissue ossification
4 external bridging calls <50% callus response zone length
5 external bridging callus >50% callus response zone length
6 partial external callus union
7 complete external callus union
8 medullar callus fusion
9 partial callus remodeling
10 complete callus remodeling.

Figure 9:
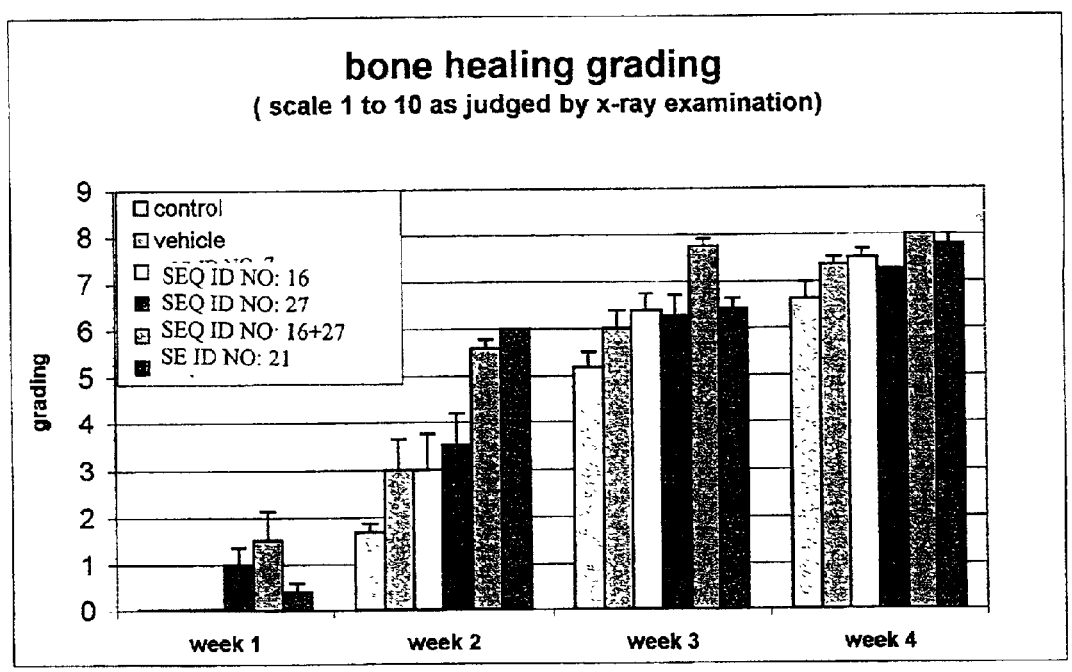
FIG. 9 illustrates the bone healing in rabbit mid-ulna osteotomies by a compound comprising ALK peptide/peptide variant (K098H101 and K099B901), a compound comprising ACR-IIR peptide/peptide variant (K095D801), and a combination of two compounds comprising two peptides—(K095D801 and K099B901 respectively).

As can be seen in FIG. 9, peptide SEQ ID NO: 21 (K098H101 in Table 1) and the combination of peptides SEQ ID NO: 16 (K095D801 in Table 1) and SEQ ID NO: 27 (K099B901 in Table 1) significantly accelerate bone healing, as soon as two weeks post operation. The histological sections for TGF-β peptides SEQ ID NO: 21 (K098H101 in Table 1) and SEQ ID NO: 27 (K099B901 in Table 1) are shown in FIGS. 10 and 11.

Figure 10A:
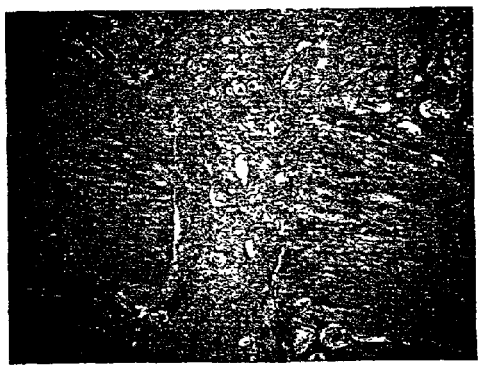
FIG. 10 illustrates the enhancement of bone remodeling in rabbit mid-ulna osteotomies by a compound comprising ALK peptide/peptide variant, (K098H101).
Figure 10B:
Figure 11A:
FIG. 11 illustrates the enhancement of bone remodeling in rabbits at the site of osteotomies by a compound comprising ALK peptide/peptide variant, (K099B901).
Figure 11B:
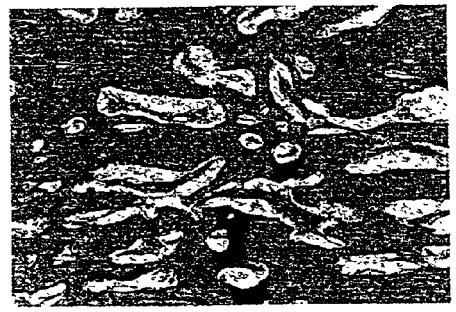

As can clearly be seen in FIGS. 10 and 11, while in the control animal a fibrotic connective tissue was formed at the fraction site, in the SEQ ID NO: 21 (K098H101 in Table 1) and SEQ ID NO: 27 (K099B901 in Table 1) treated animals, a bone like bone-tissue was formed leading to a genuine regeneration.

While this invention has been particularly shown and described with references to preferred embodiments thereof, it will be understood by those skilled in the art that various changes in from and details may be made therein without departing from the scope of the invention encompassed by the appended claims. All references, patent applications, and patents cited herein are included by reference in their entirety.

What is claimed is:

1. A method for the enhancement of bone healing in a subject comprising administering to the subject in need of such treatment a therapeutically effective amount of the compound of SEQ ID NO:21.

2. A method for increasing bone density in a subject comprising administering to the subject in need of such treatment a therapeutically effective amount of the compound of SEQ ID NO:21.

* * * * *

SEQUENCE LISTING

```
<160> NUMBER OF SEQ ID NOS: 59

<210> SEQ ID NO 1
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: palmytoyl-G

<400> SEQUENCE: 1

Xaa Ser Leu Tyr Asp Phe Leu Gln Arg Gln Thr Leu
1               5                   10

<210> SEQ ID NO 2
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 2

Xaa Thr His Tyr His Glu His Gly Ser Leu Tyr Asp Phe Leu Gln Arg
1               5                   10                  15

Gln Thr Leu

<210> SEQ ID NO 3
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
```

<223> OTHER INFORMATION: myristyl-G

<400> SEQUENCE: 3

Xaa Gly Ile Val Glu Asp Tyr Arg Pro Pro Phe
1               5                   10

<210> SEQ ID NO 4
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 4

Gly Ile Val Glu Asp Tyr Arg Pro Pro
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 5

Xaa Gly Ile Val Glu Asp Tyr Arg Pro
1               5

<210> SEQ ID NO 6
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 6

Xaa Val Asn Gly Ile Val Glu Asp Tyr Arg Pro
1               5                   10

<210> SEQ ID NO 7
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 7

Xaa Ile Ala Arg Arg Thr Ile Val Asn
1               5

<210> SEQ ID NO 8
<211> LENGTH: 12
<212> TYPE: PRT

```
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 8

Xaa Ile Ala Arg Arg Thr Ile Val Asn Gly Ile Val
1               5                   10

<210> SEQ ID NO 9
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 9

Xaa Thr Ile Val Asn Gly Ile Val
1               5

<210> SEQ ID NO 10
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: stearyl-G

<400> SEQUENCE: 10

Xaa Gly Ile Val Glu Asp Tyr Arg Pro Pro Phe
1               5                   10

<210> SEQ ID NO 11
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: stearyl-G

<400> SEQUENCE: 11

Xaa Asp Met Thr Ser Arg Asn Ser Ser Thr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: palmytoyl-G

<400> SEQUENCE: 12

Xaa Asn Leu Gln Glu Tyr Leu Thr Arg His Val Ile
```

<210> SEQ ID NO 13
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 13

Xaa Thr Ala Phe His Ala Lys Gly Asn Leu Gln Glu Tyr Leu Thr Arg
1               5                   10                  15

His Val Ile

<210> SEQ ID NO 14
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 14

Xaa Gly Glu Val Lys Asp Tyr Glu Pro Pro Phe
1               5                   10

<210> SEQ ID NO 15
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: stearyl-G

<400> SEQUENCE: 15

Xaa Gly Leu Val Thr Arg Glu Val Pro Phe
1               5                   10

<210> SEQ ID NO 16
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: palmytoyl-G

<400> SEQUENCE: 16

Xaa Ser Leu Ser Asp Phe Leu Lys Ala Asn Val Val
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic

```
<220> FEATURE:
<221> NAME/KEY: MISC_FEATURE
<222> LOCATION: (1)..(1)
<223> OTHER INFORMATION: myristyl-G
<220> FEATURE:
<221> NAME/KEY: MISC_FEATURE
<222> LOCATION: (1)..(1)
<223> OTHER INFORMATION: acetyl-G

<400> SEQUENCE: 17

Xaa Pro Val Asp Glu Tyr Met Leu Pro Phe
1               5                   10

<210> SEQ ID NO 18
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: stearyl-G

<400> SEQUENCE: 18

Xaa Glu Lys Arg Gly Ser Asn Leu Glu Val
1               5                   10

<210> SEQ ID NO 19
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: palmytoyl-G

<400> SEQUENCE: 19

Xaa Ser Leu Tyr Asp Phe Leu Lys Cys Ala Thr Leu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: palmytyol-G

<400> SEQUENCE: 20

Xaa Ser Leu Tyr Asp Phe Leu Lys Ser Ala Thr Leu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 21
```

```
Xaa Gly Ile Val Glu Glu Tyr Gln Leu Pro Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: stearyl-G

<400> SEQUENCE: 22

Xaa Gly Ile Val Glu Glu Tyr Gln Leu Pro Tyr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 23

Xaa Gly Leu Met Arg His Glu Asn Ile Leu Gly Phe
1               5                   10

<210> SEQ ID NO 24
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: stearyl-G

<400> SEQUENCE: 24

Xaa Asp Ile Lys Gly Thr Gly Ser Trp Thr
1               5                   10

<210> SEQ ID NO 25
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: palmytoyl-G

<400> SEQUENCE: 25

Xaa Ser Leu Phe Asp Tyr Leu Asn Arg Tyr Thr Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: synthetic
<220> FEATURE:
```

```
<221> NAME/KEY: MISC_FEATURE
<222> LOCATION: (1)..(1)
<223> OTHER INFORMATION: myristyl-G

<400> SEQUENCE: 26

Xaa Gly Gln Val His Glu Glu Tyr Gln Leu Pro Tyr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: stearyl-G

<400> SEQUENCE: 27

Xaa Asp Asn Lys Asp Asn Gly Thr Trp Thr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: myristyl-G

<400> SEQUENCE: 28

Xaa Leu Ser Lys Tyr Leu Ser Leu His Thr Ser
1               5                   10

<210> SEQ ID NO 29
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: acetyl-G

<400> SEQUENCE: 29

Xaa Leu Cys Lys Tyr Leu Ser Leu His Thr Ser
1               5                   10

<210> SEQ ID NO 30
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: palmytoyl-G

<400> SEQUENCE: 30

Xaa Gly Glu Ser Val Pro Glu Tyr Gln Met Ala Phe
1               5                   10

<210> SEQ ID NO 31
```

```
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: stearyl-G

<400> SEQUENCE: 31

Xaa Asp Glu Arg Val Thr Ala Asp Gly Arg Met
1               5                   10

<210> SEQ ID NO 32
<211> LENGTH: 31
<212> TYPE: PRT
<213> ORGANISM: Artificial Sequence
<220> FEATURE:
<223> OTHER INFORMATION: synthetic

<400> SEQUENCE: 32

Glu Ile Ala Arg Arg Cys Ser Ile Gly Gly Ile His Glu Asp Tyr Gln
1               5                   10                  15

Leu Pro Tyr Tyr Asp Leu Val Pro Ser Asp Pro Ser Val Glu Glu
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: synthetic

<400> SEQUENCE: 33

Glu Leu Val Ser Arg Cys Lys Ala Ala Asp Gly Pro Val Asp Glu Tyr
1               5                   10                  15

Met Leu Pro Phe Glu Glu Glu Ile Gly Gln His Pro Ser Leu Glu Glu
            20                  25                  30

<210> SEQ ID NO 34
<211> LENGTH: 34
<212> TYPE: PRT
<213> ORGANISM: Artificial Sequence
<220> FEATURE:
<223> OTHER INFORMATION: synthetic

<400> SEQUENCE: 34

Glu Ile Phe Met Arg Cys Thr Asp Leu Phe Pro Gly Glu Ser Val Pro
1               5                   10                  15

Glu Tyr Gln Met Ala Phe Gln Thr Glu Val Gly Asn His Pro Thr Phe
            20                  25                  30

Glu Asp

<210> SEQ ID NO 35
<211> LENGTH: 31
<212> TYPE: PRT
<213> ORGANISM: Artificial Sequence
<220> FEATURE:
<223> OTHER INFORMATION: synthetic

<400> SEQUENCE: 35

Glu Met Thr Ser Arg Cys Asn Ala Val Gly Glu Val Lys Asp Tyr Glu
1               5                   10                  15

Pro Pro Phe Gly Ser Lys Val Arg Glu His Pro Cys Val Glu Ser
```

```
                20                  25                  30
```

<210> SEQ ID NO 36
<211> LENGTH: 31
<212> TYPE: PRT
<213> ORGANISM: Artificial Sequence
<220> FEATURE:
<223> OTHER INFORMATION: synthetic

<400> SEQUENCE: 36

```
Glu Ile Ala Arg Arg Cys Asn Ser Gly Gly Val His Glu Glu Tyr Gln
1               5                   10                  15

Leu Pro Tyr Tyr Asp Leu Val Pro Ser Asp Pro Ser Ile Glu Glu
                20                  25                  30
```

<210> SEQ ID NO 37
<211> LENGTH: 31
<212> TYPE: PRT
<213> ORGANISM: Artificial Sequence
<220> FEATURE:
<223> OTHER INFORMATION: synthetic

<400> SEQUENCE: 37

```
Glu Met Ala Arg Arg Cys Ile Thr Gly Gly Ile Val Glu Glu Tyr Gln
1               5                   10                  15

Leu Pro Tyr Tyr Asn Met Val Pro Ser Asp Pro Ser Tyr Glu Asp
                20                  25                  30
```

<210> SEQ ID NO 38
<211> LENGTH: 31
<212> TYPE: PRT
<213> ORGANISM: Artificial Sequence
<220> FEATURE:
<223> OTHER INFORMATION: synthetic

<400> SEQUENCE: 38

```
Glu Ile Ala Arg Arg Thr Ile Val Asn Gly Ile Val Glu Asp Tyr Arg
1               5                   10                  15

Pro Pro Phe Tyr Asp Val Val Pro Asn Asp Pro Ser Phe Glu Asp
                20                  25                  30
```

<210> SEQ ID NO 39
<211> LENGTH: 21
<212> TYPE: PRT
<213> ORGANISM: Artificial Sequence
<220> FEATURE:
<223> OTHER INFORMATION: synthetic

<400> SEQUENCE: 39

```
Ser Asp Tyr His Glu His Gly Ser Leu Phe Asp Tyr Leu Asn Arg Tyr
1               5                   10                  15

Thr Val Thr Val Glu
                20
```

<210> SEQ ID NO 40
<211> LENGTH: 22
<212> TYPE: PRT
<213> ORGANISM: Artificial Sequence
<220> FEATURE:
<223> OTHER INFORMATION: synthetic

<400> SEQUENCE: 40

```
Thr Ala Phe His Asp Lys Gly Ser Leu Thr Asp Tyr Leu Lys Gly Asn
1               5                   10                  15
```

```
Ile Ile Thr Trp Asn Glu
            20

<210> SEQ ID NO 41
<211> LENGTH: 21
<212> TYPE: PRT
<213> ORGANISM: Artificial Sequence
<220> FEATURE:
<223> OTHER INFORMATION: synthetic

<400> SEQUENCE: 41

Met Glu Tyr Tyr Pro Asn Gly Ser Leu Cys Lys Tyr Leu Ser Leu His
1               5                   10                  15

Thr Ser Asp Trp Val
            20

<210> SEQ ID NO 42
<211> LENGTH: 21
<212> TYPE: PRT
<213> ORGANISM: Artificial Sequence
<220> FEATURE:
<223> OTHER INFORMATION: synthetic

<400> SEQUENCE: 42

Thr Ala Phe His Ala Lys Gly Asn Leu Gln Glu Tyr Leu Thr Arg His
1               5                   10                  15

Val Ile Ser Trp Glu
            20

<210> SEQ ID NO 43
<211> LENGTH: 21
<212> TYPE: PRT
<213> ORGANISM: Artificial Sequence
<220> FEATURE:
<223> OTHER INFORMATION: synthetic

<400> SEQUENCE: 43

Ser Asp Tyr His Glu His Gly Ser Leu Phe Asp Tyr Leu Asn Arg Tyr
1               5                   10                  15

Thr Val Thr Ile Glu
            20

<210> SEQ ID NO 44
<211> LENGTH: 21
<212> TYPE: PRT
<213> ORGANISM: Artificial Sequence
<220> FEATURE:
<223> OTHER INFORMATION: synthetic

<400> SEQUENCE: 44

Thr Asp Tyr His Glu Asn Gly Ser Leu Tyr Asp Phe Leu Lys Cys Ala
1               5                   10                  15

Thr Leu Asp Thr Arg
            20

<210> SEQ ID NO 45
<211> LENGTH: 21
<212> TYPE: PRT
<213> ORGANISM: Artificial Sequence
<220> FEATURE:
<223> OTHER INFORMATION: synthetic

<400> SEQUENCE: 45

Thr His Tyr His Glu His Gly Ser Leu Tyr Asp Phe Leu Gln Arg Gln
1               5                   10                  15
```

Thr Leu Glu Pro His
          20

<210> SEQ ID NO 46
<211> LENGTH: 17
<212> TYPE: PRT
<213> ORGANISM: Artificial Sequence
<220> FEATURE:
<223> OTHER INFORMATION: synthetic

<400> SEQUENCE: 46

Ala Asp Asn Lys Asp Asn Gly Thr Trp Thr Gln Leu Trp Leu Val Ser
1               5                   10                  15

Asp

<210> SEQ ID NO 47
<211> LENGTH: 17
<212> TYPE: PRT
<213> ORGANISM: Artificial Sequence
<220> FEATURE:
<223> OTHER INFORMATION: synthetic

<400> SEQUENCE: 47

Ala Glu Lys Arg Gly Ser Ser Leu Glu Ala Glu Leu Trp Leu Ile Thr
1               5                   10                  15

Ala

<210> SEQ ID NO 48
<211> LENGTH: 18
<212> TYPE: PRT
<213> ORGANISM: Artificial Sequence
<220> FEATURE:
<223> OTHER INFORMATION: synthetic

<400> SEQUENCE: 48

Gly Asp Glu Arg Val Thr Ala Asp Gly Arg Met Glu Tyr Leu Leu Val
1               5                   10                  15

Met Glu

<210> SEQ ID NO 49
<211> LENGTH: 17
<212> TYPE: PRT
<213> ORGANISM: Artificial Sequence
<220> FEATURE:
<223> OTHER INFORMATION: synthetic

<400> SEQUENCE: 49

Ala Glu Glu Arg Lys Thr Glu Leu Gly Lys Gln Tyr Trp Leu Ile Thr
1               5                   10                  15

Ala

<210> SEQ ID NO 50
<211> LENGTH: 17
<212> TYPE: PRT
<213> ORGANISM: Artificial Sequence
<220> FEATURE:
<223> OTHER INFORMATION: synthetic

<400> SEQUENCE: 50

Ala Asp Asn Lys Asp Asn Gly Thr Trp Thr Gln Leu Trp Leu Val Ser
1               5                   10                  15

Asp

<210> SEQ ID NO 51
<211> LENGTH: 17
<212> TYPE: PRT
<213> ORGANISM: Artificial Sequence
<220> FEATURE:
<223> OTHER INFORMATION: synthetic

<400> SEQUENCE: 51

Ala Asp Ile Lys Gly Thr Gly Ser Trp Thr Gln Leu Tyr Leu Ile Thr
1               5                   10                  15

Asp

<210> SEQ ID NO 52
<211> LENGTH: 17
<212> TYPE: PRT
<213> ORGANISM: Artificial Sequence
<220> FEATURE:
<223> OTHER INFORMATION: synthetic

<400> SEQUENCE: 52

Ser Asp Met Thr Ser Arg Asn Ser Ser Thr Gln Leu Trp Leu Ile Thr
1               5                   10                  15

His

<210> SEQ ID NO 53
<211> LENGTH: 15
<212> TYPE: PRT
<213> ORGANISM: Artificial Sequence
<220> FEATURE:
<223> OTHER INFORMATION: synthetic

<400> SEQUENCE: 53

Gln Thr Val Met Leu Arg His Glu Asn Ile Leu Gly Phe Ile Ala
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: synthetic

<400> SEQUENCE: 54

Ser Thr Pro Gly Met Lys His Glu Asn Leu Leu Gln Phe Ile Ala
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: synthetic

<400> SEQUENCE: 55

Arg Val Pro Leu Met Glu His Asp Asn Ile Ala Arg Phe Ile Val
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: synthetic

<400> SEQUENCE: 56

```
Ser Asp Ile Asn Leu Lys His Glu Asn Ile Leu Gln Phe Leu Thr
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: synthetic

<400> SEQUENCE: 57

Gln Thr Val Met Leu Arg His Glu Asn Ile Leu Gly Phe Ile Ala
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: synthetic

<400> SEQUENCE: 58

Gln Thr Val Leu Met Arg His Glu Asn Ile Leu Gly Phe Ile Ala
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: synthetic

<400> SEQUENCE: 59

Asn Thr Val Leu Leu Arg His Asp Asn Ile Leu Gly Phe Ile Ala
1               5                   10                  15
```